(12) United States Patent
O'Connor et al.

(10) Patent No.: US 11,357,660 B2
(45) Date of Patent: Jun. 14, 2022

(54) IMPLANTABLE MEDICAL DEVICES FOR TISSUE REPOSITIONING

(71) Applicants: Cook Medical Technologies LLC, Bloomington, IN (US); Cook Biotech Incorporated, West Lafayette, IN (US)

(72) Inventors: Peter O'Connor, Worcester, MA (US); Wade Colburn, West Lafayette, IN (US); Chelsea McKiernan, Lafayette, IN (US); Andrew P. Isch, West Lafayette, IN (US); Alexander Brethauer, Indianapolis, IN (US)

(73) Assignees: Cook Medical Technologies, LLC, Bloomington, IN (US); Cook Biotech Incorporated, West Lafayette, IN (US)

( * ) Notice: Subject to any disclaimer, the term of this patent is extended or adjusted under 35 U.S.C. 154(b) by 287 days.

(21) Appl. No.: 16/022,655

(22) Filed: Jun. 28, 2018

(65) Prior Publication Data

US 2019/0000661 A1  Jan. 3, 2019

Related U.S. Application Data

(60) Provisional application No. 62/526,522, filed on Jun. 29, 2017.

(51) Int. Cl.
| | | |
|---|---|---|
| *A61F 5/56* | (2006.01) | |
| *A61F 2/82* | (2013.01) | |
| *A61B 5/00* | (2006.01) | |
| *A61F 2/20* | (2006.01) | |

(52) U.S. Cl.
CPC ............... *A61F 5/566* (2013.01); *A61F 2/82* (2013.01); *A61B 5/4818* (2013.01); *A61F 2/20* (2013.01)

(58) Field of Classification Search
CPC .................. A61F 2005/563; A61B 5/4818
USPC ........................ 128/848; 600/37; 606/151
See application file for complete search history.

(56) References Cited

U.S. PATENT DOCUMENTS

| | | |
|---|---|---|
| 4,024,859 A | 5/1977 | Slepyan et al. |
| 4,064,873 A | 12/1977 | Swenson |
| 4,608,972 A | 9/1986 | Small |
| 4,917,604 A | 4/1990 | Small |

(Continued)

FOREIGN PATENT DOCUMENTS

| | | |
|---|---|---|
| CA | 2971233 | 6/2016 |
| WO | WO200145765 | 6/2001 |

(Continued)

OTHER PUBLICATIONS

Britannica, The Editors of Encyclopaedia. "Curve". Encyclopedia Britannica, Mar. 21, 2012, https://www.britannica.com/science/curve. Accessed Mar. 22, 2021. (Year: 2012).*

(Continued)

*Primary Examiner* — Keri J Nelson
*Assistant Examiner* — Trisha Talapatra
(74) *Attorney, Agent, or Firm* — MacMillan, Sobanski & Todd, LLC

(57) ABSTRACT

A medical device for repositioning tissue within an animal has a main body with a first end portion, a second end portion, and a middle portion. The first end portion defines a series of passageways and the second end portion defines a bulbous shape, a slot, and a tab portion. Methods of treating obstructive sleep apnea are also described.

21 Claims, 9 Drawing Sheets

(56) References Cited

U.S. PATENT DOCUMENTS

| | | | |
|---|---|---|---|
| 5,217,494 A * | 6/1993 | Coggins | A61F 2/0059 623/23.72 |
| 5,674,191 A | 10/1997 | Edwards et al. | |
| 5,988,171 A | 11/1999 | Sohn et al. | |
| 6,042,534 A | 3/2000 | Gellman et al. | |
| 6,159,208 A | 12/2000 | Hovda et al. | |
| 6,161,541 A | 12/2000 | Woodson | |
| 6,397,841 B1 | 6/2002 | Kenyon et al. | |
| 6,408,851 B1 | 6/2002 | Karell | |
| 6,513,530 B2 | 2/2003 | Knudson et al. | |
| 6,513,531 B2 | 2/2003 | Knudson et al. | |
| 6,523,541 B2 | 2/2003 | Knudson et al. | |
| 6,596,004 B1 | 7/2003 | Regnault | |
| 6,895,963 B1 | 5/2005 | Martin et al. | |
| 6,910,483 B2 | 6/2005 | Daly et al. | |
| 6,911,002 B2 | 6/2005 | Fierro | |
| 6,955,172 B2 | 10/2005 | Nelson et al. | |
| 6,974,419 B1 | 12/2005 | Voss et al. | |
| 7,004,941 B2 | 2/2006 | Tvinnereim et al. | |
| 7,047,979 B2 | 5/2006 | Conrad et al. | |
| 7,063,089 B2 | 6/2006 | Knudson et al. | |
| 7,073,505 B2 | 7/2006 | Nelson et al. | |
| 7,090,672 B2 | 8/2006 | Underwood et al. | |
| 7,128,069 B2 | 10/2006 | Farrugia et al. | |
| 7,168,429 B2 | 1/2007 | Matthews et al. | |
| 7,188,627 B2 | 3/2007 | Nelson et al. | |
| 7,213,599 B2 | 5/2007 | Conrad et al. | |
| 7,216,647 B2 | 5/2007 | Lang et al. | |
| 7,255,109 B2 | 8/2007 | Knudson et al. | |
| 7,291,112 B2 | 11/2007 | Martin et al. | |
| 7,337,778 B2 | 3/2008 | Martin et al. | |
| 7,337,781 B2 | 3/2008 | Vassallo | |
| 7,360,542 B2 | 4/2008 | Nelson et al. | |
| 7,363,926 B2 | 4/2008 | Pflueger et al. | |
| 7,387,634 B2 | 6/2008 | Benderev | |
| 7,401,611 B2 | 7/2008 | Conrad et al. | |
| 7,491,200 B2 | 2/2009 | Underwood | |
| 7,607,439 B2 | 10/2009 | Li | |
| 7,644,714 B2 | 1/2010 | Atkinson et al. | |
| 7,658,192 B2 | 2/2010 | Harrington | |
| 7,669,603 B2 | 3/2010 | Knudson et al. | |
| 7,673,635 B2 | 3/2010 | Conrad et al. | |
| 7,680,538 B2 | 3/2010 | Durand et al. | |
| 7,703,460 B2 | 4/2010 | Conrad et al. | |
| 7,813,812 B2 | 10/2010 | Kieval et al. | |
| 7,827,038 B2 | 11/2010 | Richard et al. | |
| 7,827,988 B2 | 11/2010 | Matthews et al. | |
| 7,845,357 B2 | 12/2010 | Buscemi et al. | |
| 7,856,980 B2 | 12/2010 | Lang et al. | |
| 7,874,291 B2 | 1/2011 | Ging et al. | |
| 7,884,101 B2 | 2/2011 | Teegarden et al. | |
| 7,909,037 B2 | 3/2011 | Hegde et al. | |
| 7,909,038 B2 | 3/2011 | Hedge et al. | |
| 7,921,850 B2 | 4/2011 | Nelson et al. | |
| 7,934,506 B2 | 5/2011 | Woodson et al. | |
| 7,935,065 B2 | 5/2011 | Martin et al. | |
| 7,938,114 B2 | 5/2011 | Matthews et al. | |
| 7,949,400 B2 | 5/2011 | Kieval et al. | |
| 7,954,494 B1 | 6/2011 | Connor | |
| 7,955,267 B2 | 6/2011 | Voss et al. | |
| 7,959,554 B2 | 6/2011 | McAlexander et al. | |
| 7,975,700 B2 | 7/2011 | Frazier et al. | |
| 7,976,471 B2 | 7/2011 | Martin et al. | |
| 7,980,248 B2 | 7/2011 | Hedge et al. | |
| 7,992,564 B2 | 8/2011 | Doshi et al. | |
| 7,992,566 B2 | 8/2011 | Pflueger et al. | |
| 7,992,567 B2 | 8/2011 | Hirotsuka et al. | |
| 7,997,266 B2 | 8/2011 | Frazier et al. | |
| 7,997,267 B2 | 8/2011 | Ging et al. | |
| 8,020,560 B2 | 9/2011 | Paraschac et al. | |
| 8,074,655 B2 | 12/2011 | Sanders | |
| 8,096,303 B2 | 1/2012 | Dineen et al. | |
| 8,167,787 B2 | 5/2012 | Gillis | |
| 8,186,355 B2 | 5/2012 | van der Burg et al. | |
| 8,220,466 B2 | 7/2012 | Frazier et al. | |
| 8,220,467 B2 | 7/2012 | Sanders | |
| 8,327,854 B2 | 12/2012 | Gillis et al. | |
| 8,460,322 B2 | 6/2013 | van der Burg et al. | |
| 8,776,799 B2 | 7/2014 | Gillis et al. | |
| 8,932,325 B2 | 1/2015 | Stanley et al. | |
| 8,936,616 B2 | 1/2015 | Nelson | |
| 9,867,733 B2 | 1/2018 | Mohan et al. | |
| 2001/0050085 A1 | 12/2001 | Knudson et al. | |
| 2003/0111079 A1 | 6/2003 | Matthews et al. | |
| 2003/0140925 A1 | 7/2003 | Sapienza et al. | |
| 2003/0168064 A1 | 9/2003 | Daly et al. | |
| 2003/0176875 A1 | 9/2003 | Anderson et al. | |
| 2004/0006353 A1 | 1/2004 | Bosley, Jr. et al. | |
| 2004/0028676 A1 | 2/2004 | Klein et al. | |
| 2004/0073272 A1 | 4/2004 | Knudson et al. | |
| 2004/0112387 A1 | 6/2004 | Lang et al. | |
| 2004/0144395 A1 | 7/2004 | Evans et al. | |
| 2004/0153127 A1 | 8/2004 | Gordon et al. | |
| 2004/0187870 A1 | 9/2004 | Matthews et al. | |
| 2004/0231678 A1 | 11/2004 | Fierro | |
| 2005/0005937 A1 | 1/2005 | Farrugia et al. | |
| 2005/0098184 A1 | 5/2005 | Conrad et al. | |
| 2005/0103339 A1 | 5/2005 | Daly et al. | |
| 2005/0126563 A1 | 6/2005 | van der Burg et al. | |
| 2005/0175665 A1 | 8/2005 | Hunter et al. | |
| 2005/0178384 A1 | 8/2005 | Martin et al. | |
| 2005/0217673 A1 | 10/2005 | Daly et al. | |
| 2005/0267547 A1 | 12/2005 | Knudson et al. | |
| 2005/0279365 A1 | 12/2005 | Armijo et al. | |
| 2006/0000475 A1 | 1/2006 | Matthews et al. | |
| 2006/0070626 A1 | 4/2006 | Frazier et al. | |
| 2006/0150986 A1 | 7/2006 | Roue et al. | |
| 2006/0207612 A1 | 9/2006 | Jackson et al. | |
| 2006/0235877 A1 | 10/2006 | Richard et al. | |
| 2007/0132117 A1 | 6/2007 | Truitt et al. | |
| 2007/0134085 A1 | 6/2007 | Daly et al. | |
| 2007/0144539 A1 | 6/2007 | van der Burg et al. | |
| 2007/0157928 A1 | 7/2007 | Pujol et al. | |
| 2007/0157934 A1 | 7/2007 | Lang et al. | |
| 2007/0207994 A1 | 9/2007 | Teegarden et al. | |
| 2007/0209664 A1 | 9/2007 | Paraschac et al. | |
| 2007/0209665 A1 | 9/2007 | Gillis et al. | |
| 2007/0244086 A1 | 10/2007 | Teegarden et al. | |
| 2007/0256693 A1 | 11/2007 | Paraschac et al. | |
| 2007/0287923 A1 | 12/2007 | Adkins et al. | |
| 2008/0023012 A1 | 1/2008 | Dineen et al. | |
| 2008/0027560 A1 | 1/2008 | Jackson et al. | |
| 2008/0041382 A1 | 2/2008 | Matthews et al. | |
| 2008/0041383 A1 | 2/2008 | Matthews et al. | |
| 2008/0045813 A1 | 2/2008 | Phuah et al. | |
| 2008/0053461 A1 | 3/2008 | Kirotsuka et al. | |
| 2008/0058584 A1 | 3/2008 | Hirotsuka et al. | |
| 2008/0066753 A1 | 3/2008 | Martin et al. | |
| 2008/0066765 A1 | 3/2008 | Paraschac et al. | |
| 2008/0066769 A1 | 3/2008 | Dineen et al. | |
| 2008/0091058 A1 | 4/2008 | Bosley et al. | |
| 2008/0097380 A1 | 4/2008 | Li | |
| 2008/0099019 A1 | 5/2008 | Martin et al. | |
| 2008/0194953 A1 | 8/2008 | Kerber | |
| 2008/0208265 A1 | 8/2008 | Frazier et al. | |
| 2008/0251071 A1 | 10/2008 | Armitstead et al. | |
| 2009/0044814 A1 | 2/2009 | Iancea et al. | |
| 2009/0053306 A1 | 2/2009 | Agarwal et al. | |
| 2009/0060905 A1 | 3/2009 | Martin et al. | |
| 2009/0099471 A1 | 4/2009 | Broadley et al. | |
| 2009/0131923 A1 | 5/2009 | Connors et al. | |
| 2010/0004264 A1 | 1/2010 | Xiong et al. | |
| 2010/0010061 A1 | 1/2010 | Cooper et al. | |
| 2010/0016694 A1 | 1/2010 | Martin et al. | |
| 2010/0028026 A1 | 2/2010 | Inami et al. | |
| 2010/0106246 A1 | 4/2010 | Rousseau et al. | |
| 2010/0108066 A1 | 5/2010 | Martin et al. | |
| 2010/0108077 A1 | 5/2010 | Lindh et al. | |
| 2010/0132719 A1 | 6/2010 | Jacobs et al. | |
| 2010/0144701 A1 | 6/2010 | Cooper et al. | |
| 2010/0234946 A1 | 9/2010 | Rousseau | |
| 2010/0300458 A1 | 12/2010 | Stubbs et al. | |
| 2011/0056498 A1 | 3/2011 | Lang et al. | |
| 2011/0094520 A1 | 4/2011 | Mikhailenok et al. | |

(56) References Cited

U.S. PATENT DOCUMENTS

| | | | |
|---|---|---|---|
| 2011/0100376 A1 | 5/2011 | Rousseau | |
| 2011/0100378 A1 | 5/2011 | Rousseau | |
| 2011/0130249 A1 | 6/2011 | Mikhailenok et al. | |
| 2011/0144421 A1 | 6/2011 | Gillis et al. | |
| 2011/0166673 A1 | 7/2011 | Patel et al. | |
| 2011/0183928 A1 | 7/2011 | Thede et al. | |
| 2011/0226264 A1 | 9/2011 | Friedman et al. | |
| 2011/0245850 A1 | 10/2011 | van der Burg et al. | |
| 2011/0288368 A1* | 11/2011 | VanDeWeghe | A61F 2/0022 600/30 |
| 2011/0308530 A1 | 12/2011 | Gillis et al. | |
| 2012/0053617 A1 | 3/2012 | Benz et al. | |
| 2012/0132214 A1 | 5/2012 | Gillis et al. | |
| 2012/0157761 A1* | 6/2012 | Crank | A61B 17/2812 600/37 |
| 2013/0035543 A1* | 2/2013 | Fischer | A61F 2/0045 600/37 |
| 2013/0056009 A1 | 3/2013 | Mohan et al. | |
| 2013/0085546 A1 | 4/2013 | Bolea et al. | |
| 2013/0180528 A1 | 7/2013 | Zhou et al. | |
| 2013/0213409 A1 | 8/2013 | Podmore et al. | |
| 2014/0000631 A1* | 1/2014 | Gillis | A61F 5/566 128/848 |
| 2014/0102460 A1 | 4/2014 | Catalano | |
| 2014/0155687 A1* | 6/2014 | Goldman | A61F 2/0063 600/30 |
| 2014/0316445 A1 | 10/2014 | Shah et al. | |
| 2015/0034095 A1 | 2/2015 | Mohan et al. | |
| 2015/0157327 A1 | 6/2015 | Hoeglund | |
| 2015/0202074 A1 | 7/2015 | Gillis et al. | |
| 2018/0153732 A1 | 6/2018 | Bronikowski et al. | |

FOREIGN PATENT DOCUMENTS

| | | |
|---|---|---|
| WO | WO2003002027 | 1/2003 |
| WO | WO2007149469 | 12/2007 |
| WO | WO2009140197 | 11/2009 |
| WO | WO2010045546 | 4/2010 |
| WO | WO2010051195 | 5/2010 |
| WO | WO2011068952 | 6/2011 |
| WO | WO2011123714 | 10/2011 |
| WO | WO2011146729 | 11/2011 |
| WO | WO2013010169 | 1/2013 |
| WO | WO2014189540 | 11/2014 |

OTHER PUBLICATIONS

International Bureau of WIPO. International Preliminary Report on Patentability, dated Dec. 31, 2019, pp. 1-7.
International Searching Authority, International Search Report and the Written Opinion, for International Application No. PCT/US2012/046923, dated Nov. 2, 2012, p. 1-18.
File history of U.S. Appl. No. 08/883,220, now U.S. Pat. No. 5,988,171, as of Nov. 21, 2013, filed Jun. 26, 1997. First Named Inventor, Ze'ev Sohn. Title, Methods and Devices for the Treatment of Airway Obstruction, Sleep Apnea and Snoring.
File history of U.S. Appl. No. 10/877,003, now U.S. Pat. No. 7,213,599, as of Nov. 21, 2013, filed Jun. 24, 2004. First Named Inventor, Timothy R. Conrad. Title, Airway Implant.
File history of U.S. Appl. No. 11/757,501, now U.S. Pat. No. 7,703,460, as of Nov. 21, 2013, filed Jun. 4, 2007. First Named Inventor, Timothy R. Conrad. Title, Tongue Implant.
File history of U.S. Appl. No. 12/214,084 as of Nov. 21, 2013, filed Jun. 17, 2008. First Named Inventor, Octavian Iancea. Title, Implantable devices, systems, and methods for maintaining desired orientations in targeted tissue regions.
Woodson et al. Multicenter study of a novel adjustable tongue-advancement device for obstructive sleep apnea [article]. Otolaryngology—head and neck surgery, vol. 143, No. 4, pp. 585-590. IP: 128.210.125.135. Jun. 10, 2010. SAGE.
Woodson et al. Response to: Multicenter study of a novel adjustable tongue-advancement device for obstructive sleep apnea [article]. Otolaryngology—head and neck surgery, vol. 144, No. 6, pp. 1009-1012. 2011. SAGE.
Siesta Medical. Siesta Medical receives 510(k) clearance for Encore system to treat obstructive sleep apnea [press release], Sep. 12, 2011. pp. 1-2.
Aspire Medical, Inc. Aspire Medical announces first implant in US and start of clinical trial to treat sleep apnea [article]. Medical News Today. May 23, 2007. pp. 1-4. URL: <http://www.medicalnewstoday.com/releases/71787.php>.
Hamans et al. A novel tongue implant for tongue advancement for obstructive sleep apnea: feasibility, safety and histology in a canine model [article]. J Musculoskelet Neuronal Interact. vol. 10, No. 1, pp. 100-111. Dec. 29, 2009. Hylonome.
Knobbe, Martens, Olson & Bear, LLP. Amendment and response to non-Final Office Action dated Jan. 16, 2013, for U.S. Appl. No. 13/077,813, filed Mar. 31, 2011. First Named Inventor, van der Burg. Title, Suture Passer Systems and Methods for Tongue or Other Tissue Suspension and Compression.
PR Newswire. Asprie Medical appoints Roseanne Varner as president and CEO [press release]. pp. 1-2. May 1, 2011. URL: <http://www.prnewswire.com/news-releases/aspire-medical-appoints-roseanne-varner-as-president-and-ceo-57760852.html>.
Park. Aspire Medical Advance System for obstructive sleep apnea [blog]. Dr. Park: Breathe better, sleep better, live better. pp. 1-4. Oct. 6, 2010. URL: <http://doctorstevenpark.com/aspire-medical-advance-system-for-obstructive-sleep-apnea>.
Revent Medical. The Revent Solution: Tongue Implanter Kit [webpage], 2014. pp. 1-2. Retrieved Aug. 12, 2014. URL: <http://www.reventmedical.com/solution/>.
Revent Medical. The Revent Solution: Implants [webpage]. 2014. pp. 1-2. Retrieved Aug. 12, 2014. URL: <www.reventmedical.com/solution/>.
Australian Government—IP Australia, "Examination report No. 1 for standard patent application," for Application No. 2014296053, dated Apr. 16, 2018; pp. 1-5.
International Searching Authority, International Search Report and the Written Opinion, for International Application No. PCT/US2014/049341, dated Nov. 19, 2014, p. 1-11.
European Patent Office, "Extended European Search Report," for Application No. EP16150647.2, dated Apr. 12, 2016; pp. 1-7.
International Searching Authority. International Search Report and Written Opinion of the International Searching Authority, for International App. No. PCT/US2018/040156, dated Sep. 3, 2018.
IP Australia Examination Report No. 1 for Australian application No. 2018294247, dated Aug. 21, 2020, pp. 1-7.

* cited by examiner

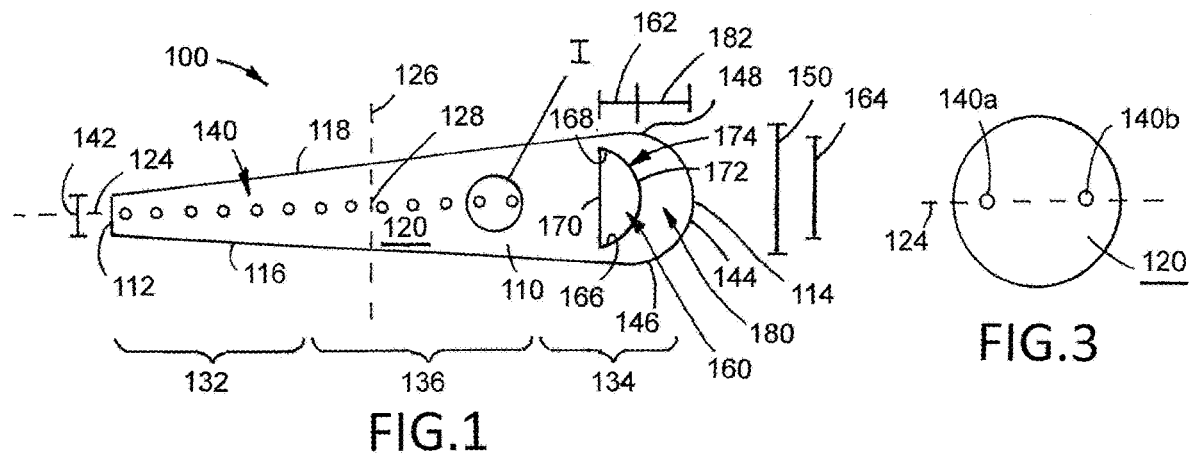
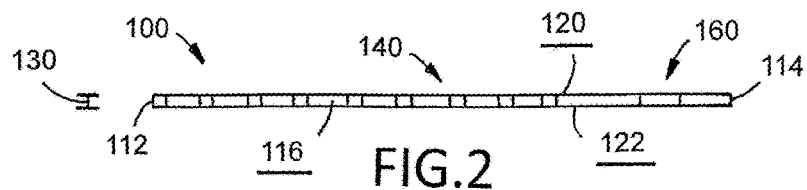
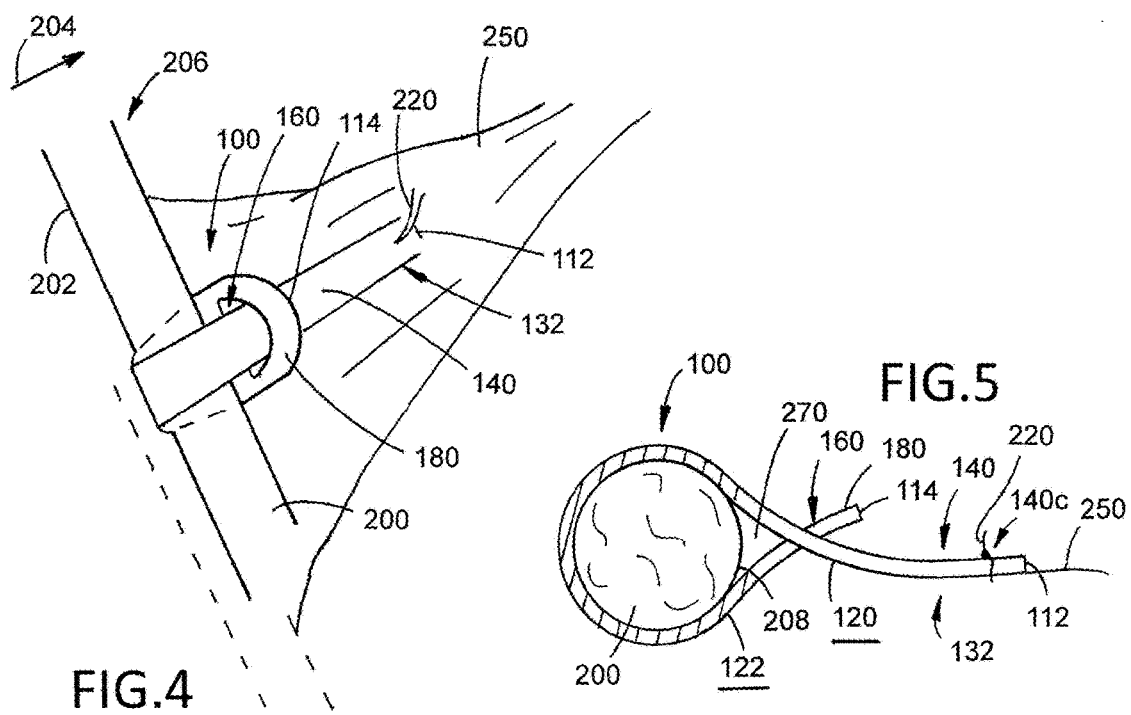

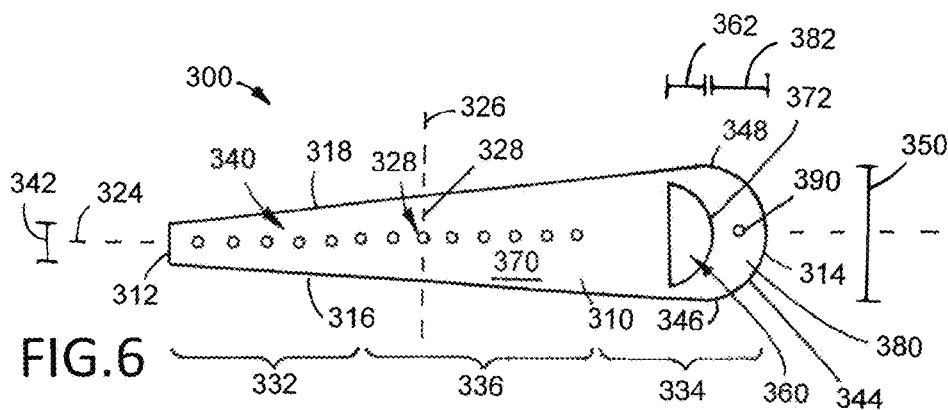
FIG.6
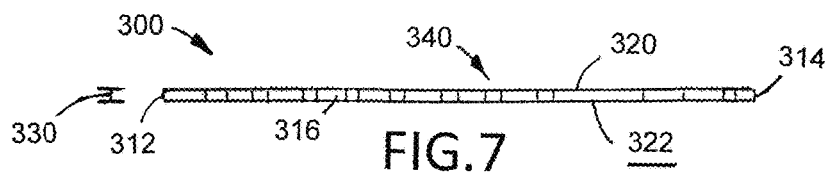
FIG.7
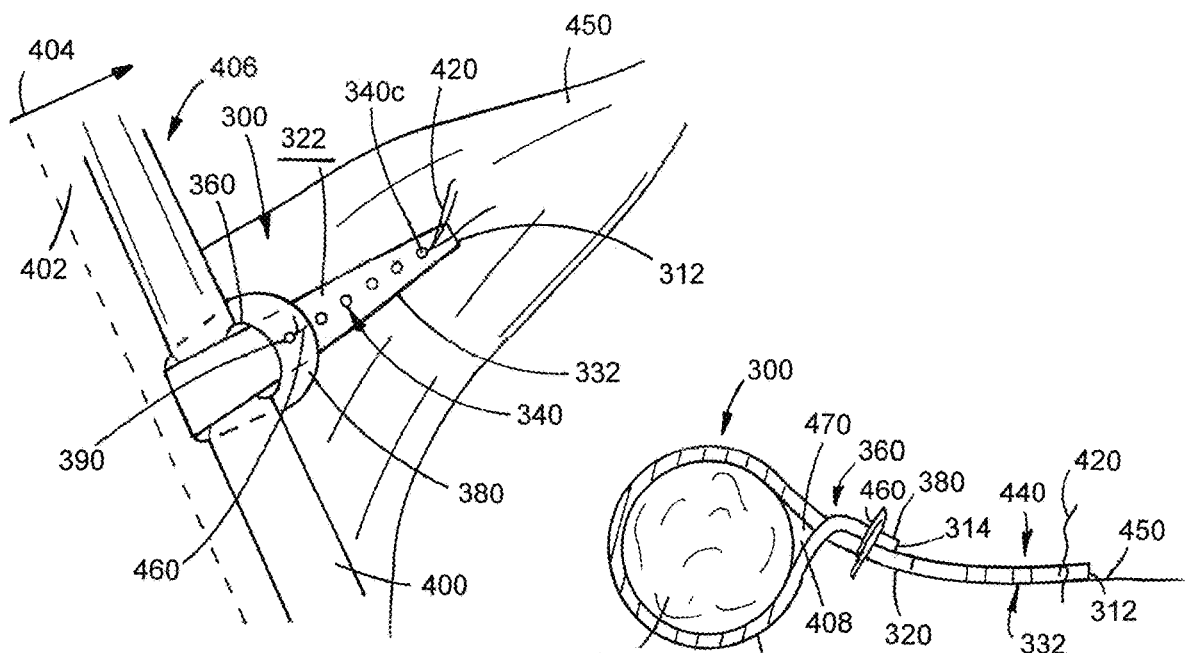
FIG.8
FIG.9

IMPLANTABLE MEDICAL DEVICES FOR TISSUE REPOSITIONING

FIELD

The disclosure relates to the field of medical devices. More particularly, the disclosure relates to implantable medical devices useful for repositioning tissue within an animal, such as a human. Specific examples relate to implantable medical devices for repositioning a palatopharyngeus muscle in the treatment of obstructive sleep apnea. The invention also relates to methods of treating obstructive sleep apnea.

BACKGROUND

It is sometimes necessary or desirable to reposition a tissue or portion of a tissue within the body of an animal, such as a human, to accomplish a treatment objective. For example, in the treatment of obstructive sleep apnea, it may be desirable to adjust the position of one or more tissues or portions of tissue, such as a palatopharyngeus muscle of a patient suffering from obstructive sleep apnea.

Obstructive sleep apnea, sometimes referred to as OSA, is a clinical disorder in which a partial or complete collapse of soft tissue occurs in the airway during sleep. This leads to a blockage of the airway and impaired breathing during sleep. Left untreated, obstructive sleep apnea can lead to fatigue, reduced alertness following sleep, and a general reduction in productivity for the affected individual. More severe obstructive sleep apnea is associated with sleep deprivation, hypoxemia, increased morbidity including elevated risk for cardiovascular disease and stroke, and depression.

Several anatomic factors can contribute to the development of obstructive sleep apnea, individually or collectively, including tongue and soft palate obstruction of the airway. Enlargement and/or collapse of the palatopharyngeus muscles can also obstruct the airway and contribute to the development of obstructive sleep apnea. This muscle contracts to move the pharynx during swallowing to prevent the bolus from entering the nasopharynx. Together with the mucous membrane that covers its entire surface, the palatopharyngeus muscle forms the palatopharyngeus arch.

Treating obstructive sleep apnea that stems in whole or in part from airway obstruction by the palatopharyngeus muscle presents challenges that are different than those associated with treating obstructive sleep apnea related to tongue and/or soft palate associated airway obstruction, particularly due to the location and function of the muscle. Collapse may include the level of the palate and retropalatal airway and more inferiorly at the level of the oropharynx. Indeed, currently available treatments for obstructive sleep apnea having a palatopharyngeus muscle component, which focus on surgical alteration of the muscle, may result in difficulty in swallowing, undesirable scarring, altering the anatomy, and other drawbacks. Furthermore, these techniques frequently do not provide a desired degree of airway clearance. Considering the possibility that surgery may provide insufficient clearance and leave the patient with swallowing and/or other new challenges, currently available approaches do not provide a clear path to successful treatment for people suffering with obstructive sleep apnea.

A need exists, therefore, for new and improved approaches to the treatment of obstructive sleep apnea associated with airway obstruction caused by the palatopharyngeus muscle. A need also exists for new and improved medical devices for repositioning tissue within an animal.

BRIEF DESCRIPTION OF SELECTED EXAMPLES

Medical devices useful in the repositioning of tissue within an animal are described.

An example medical device comprises a main body having a lengthwise axis, a first terminal end, an opposing second terminal end, a first side, a second opposing side, a first surface, a second opposing surface, and a longitudinal midpoint disposed on the lengthwise axis between the first terminal end and the second terminal end and between the first side and the second side, the second terminal end defining an arc that extends from a first arc base on the first side to a second arc base on the second side, the main body having a first width at the first terminal end extending orthogonally to the longitudinal axis from the first side to the second side, and a second width extending orthogonally to the longitudinal axis from the first arc base on the first side to the second arc base on the second side; the main body defining a first end portion extending along the lengthwise axis from the first terminal end toward but not to the longitudinal midpoint, a second end portion extending along the lengthwise axis from the second terminal end toward but not to the longitudinal midpoint, and a middle portion extending along the lengthwise axis between the first end portion and second end portion and including the longitudinal midpoint; the first end portion of the main body defining a series of passageways, each passageway of the series of passageways extending through the main body from the first surface to the second surface; the second end portion and the middle portion of the main body being free of any passageways extending through the main body from the first surface to the second surface; and the second end portion of the main body defining a semi-circular slot extending through the main body from the first surface to the second surface and having a first slot edge and a second slot edge, and a tab portion extending between the second slot edge and the second terminal end of the main body.

Another example medical device comprises a main body having a lengthwise axis, a first terminal end, an opposing second terminal end, a first side, a second opposing side, a first surface, a second opposing surface, and a longitudinal midpoint disposed on the lengthwise axis between the first terminal end and the second terminal end and between the first side and the second side, the second terminal end defining an arc that extends from a first arc base on the first side to a second arc base on the second side, the main body having a first width at the first terminal end extending orthogonally to the longitudinal axis from the first side to the second side, and a second width extending orthogonally to the longitudinal axis from the first arc base on the first side to the second arc base on the second side; the main body defining a first end portion extending along the lengthwise axis from the first terminal end toward but not to the longitudinal midpoint, a second end portion extending along the lengthwise axis from the second terminal end toward but not to the longitudinal midpoint, and a middle portion extending along the lengthwise axis between the first end portion and second end portion and including the longitudinal midpoint; the first end portion of the main body defining a series of passageways, each passageway of the series of passageways extending through the main body from the first surface to the second surface; the second end portion and the middle portion of the main body being free of any passageways extending through the main body from the first surface to the second surface; and the second end portion of the main body defining a semi-ovular slot extending through the main body from the first surface to the second surface and having a first slot edge and a second slot edge, and a tab portion extending between the second slot edge and the second terminal end of the main body.

Another example medical device comprises a main body having a lengthwise axis, a first terminal end, an opposing second terminal end, a first side, a second opposing side, a first surface, a second opposing surface, and a longitudinal midpoint disposed on the lengthwise axis between the first terminal end and the second terminal end and between the first side and the second side, the second terminal end defining an arc that extends from a first arc base on the first side to a second arc base on the second side, the main body having a first width at the first terminal end extending orthogonally to the longitudinal axis from the first side to the second side, and a second width extending orthogonally to the longitudinal axis from the first arc base on the first side to the second arc base on the second side; the main body defining a first end portion extending along the lengthwise axis from the first terminal end toward but not to the longitudinal midpoint, a second end portion extending along the lengthwise axis from the second terminal end toward but not to the longitudinal midpoint, and a middle portion extending along the lengthwise axis between the first end portion and second end portion and including the longitudinal midpoint; the first end portion of the main body defining a series of passageways, each passageway of the series of passageways extending through the main body from the first surface to the second surface; the second end portion and the middle portion of the main body being free of any passageways extending through the main body from the first surface to the second surface; and the second end portion of the main body defining a rectangular slot extending through the main body from the first surface to the second surface and having a first slot edge and a second slot edge, and a tab portion extending between the second slot edge and the second terminal end of the main body.

Another example medical device comprises a main body having a lengthwise axis, a first terminal end, an opposing second terminal end, a first side, a second opposing side, a first surface, a second opposing surface, and a longitudinal midpoint disposed on the lengthwise axis between the first terminal end and the second terminal end and between the first side and the second side, the second terminal end defining an arc that extends from a first arc base on the first side to a second arc base on the second side, the main body having a first width at the first terminal end extending orthogonally to the longitudinal axis from the first side to the second side, and a second width extending orthogonally to the longitudinal axis from the first arc base on the first side to the second arc base on the second side; the main body defining a first end portion extending along the lengthwise axis from the first terminal end toward but not to the longitudinal midpoint, a second end portion extending along the lengthwise axis from the second terminal end toward but not to the longitudinal midpoint, and a middle portion extending along the lengthwise axis between the first end portion and second end portion and including the longitudinal midpoint; the first end portion of the main body defining a series of passageways, each passageway of the series of passageways extending through the main body from the first surface to the second surface; and the second end portion of the main body defining a bulbous shape, a slot extending through the main body from the first surface to the second surface and having a first slot edge and a second slot edge, and a tab portion extending between the second slot edge and the second terminal end of the main body.

Methods for treating obstructive sleep apnea are also described.

An example method of treating obstructive sleep apnea comprises creating a mucosal incision in the arch of the posterior tonsillar pillar to expose the palatopharyngeus muscle, or removing the tonsils if desirable; isolating the palatopharyngeus muscle from the mucosa to create a clearance behind the palatopharyngeus muscle; inserting one end of a medical device according to an embodiment into the clearance; wrapping the medical device around the palatopharyngeus muscle; passing one end of the medical device through the slot of the medical device; pulling one end of the medical device to create a snug fit of the medical device around the palatopharyngeus muscle; placing the end of the medical device that was passed through the slot into the palatoglossus muscle toward the hammulus; placing a suture through a passageway through the main body of the medical device; and securing the suture to tissue to lateralize the palatopharyngeus muscle.

Another example method of treating obstructive sleep apnea comprises palpating the soft palate to ensure no evidence of a submucosal cleft is found; creating a mucosal incision in the arch of the posterior tonsillar pillar to expose the palatopharyngeus muscle, or removing the tonsils if desirable; isolating the palatopharyngeus muscle to create a clearance behind the palatopharyngeus muscle; inserting one side of a medical device according to an embodiment into to the clearance; wrapping the medical device around the palatopharyngeus muscle; passing one end of the medical device through the slot of the medical device; pulling one end of the medical device to create a snug fit of the medical device around the palatopharyngeus muscle; placing a suture through a passageway through the main body of the medical device near the narrow end of the medical device; advancing the narrow end of the medical device deep to the palatoglossus muscle toward the hammulus; retrieving a needle from the mucosa overlying the hammulus; reintroducing the needle into the mucosa and tunneling medially in the submucosa toward the mucosal incision; securing the suture to tissue to lateralize the palatopharyngeus muscle; and closing the incision with a suitable closure device, such as one or more sutures.

Additional understanding of the inventive medical devices and their use can be obtained by reviewing the detailed description of selected examples, below, with reference to the appended drawings.

DESCRIPTION OF FIGURES

FIG. 1 is a top view of a first example medical device.

FIG. 2 is an elevation view of the first example medical device.

FIG. 3 is a magnified view of area I referenced in FIG. 1.

FIG. 4 is a perspective view of the first example medical device disposed around a palatopharyngeus muscle.

FIG. 5 is a sectional view of the first example medical device disposed around a palatopharyngeus muscle.

FIG. 6 is a top view of a second example medical device.

FIG. 7 is an elevation view of the second example medical device.

FIG. 8 is a perspective view of the second example medical device disposed around a palatopharyngeus muscle.

FIG. 9 is a sectional view of the second example medical device disposed around a palatopharyngeus muscle.

DETAILED DESCRIPTION OF SELECTED EXAMPLES

Figure 10:
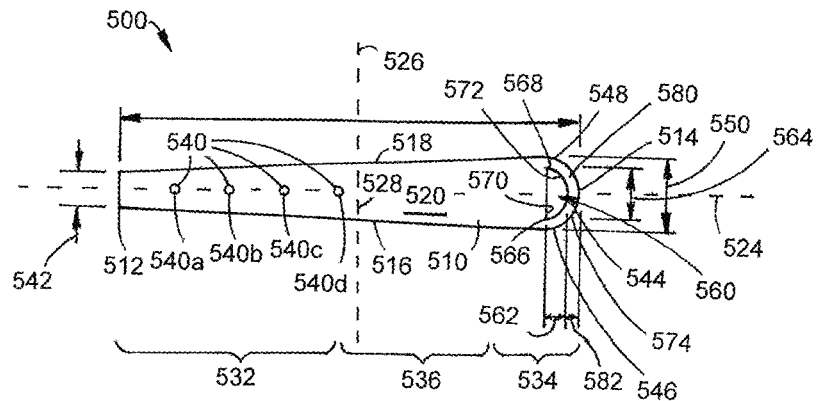
FIG. 10 is a top view of a third example medical device.

The following detailed description and the appended drawings describe and illustrate various example medical devices and methods for their use. The description and illustration of these examples are provided to enable one skilled in the art to make and use the inventive medical devices and to perform the inventive methods of their use. They are not intended to limit the scope of the protection sought or provided in any manner.

As used herein, the term 'slot' refers to a passageway that extends through the entire thickness of a member. The term does not require any particular size, shape, or configuration of the passageway.

FIGS. 1 through 3 illustrate a first example medical device 100. The medical device 100 is a sling that is suitable for repositioning the palatopharyngeus muscle of an animal, such as a human. The medical device 100 has a main body 110 comprising a substantially flat member extending from a first terminal end 112 to an opposing second terminal end 114 and having first 116 and second 118 opposing sides. The main body 110 has a first 120 or upper surface and an opposing second 122 or lower surface. The main body 110 has a lengthwise axis 124 and a transverse axis 126 that orthogonally intersects the lengthwise axis 124 at a longitudinal midpoint 128 disposed on the lengthwise axis 124. The main body has a thickness 130 measured from the first surface 120 to the opposing second surface 122. A first end portion 132 extends along the lengthwise axis 124, includes the first terminal end 112, and extends toward but not to the longitudinal midpoint 128. A second end portion 134 extends along the lengthwise axis 124, includes the second terminal end 114, and extends toward but not to the longitudinal midpoint 128. A middle portion 136 extends along the lengthwise axis 124, between the first end portion 132 and second end portion 134, and includes the longitudinal midpoint 128.

The main body 110 defines a series of passageways 140. Each passageway of the series of passageways 140 extends through the entire thickness 130 of the main body 110, from the first surface 120 to the second surface 122. FIG. 3 shows first 140a and second 140b passageways of the series of passageways 140. In the illustrated embodiment, both the first end portion 132 and the middle portion 136 includes passageways of the series of passageways 140, while the second end portion 134 is free of passageways of the series of passageways 140. In some embodiments, it may be desirable to include a middle portion that is also free of passageways of the series of passageways.

The main body 110 has a first width 142 at the first terminal end 112 that extends orthogonally to the longitudinal axis 124 from the first side 116 to the second side 118. The second terminal end 114 defines an arc 144 that extends from a first arc base 146 on the first side 116 to a second arc base 148 on the second side 118. The main body 110 has a second width 150 that extends orthogonally to the longitudinal axis 124 from the first arc base 146 on the first side 116 to the second arc base 148 on the second side 118. The second width 150 is greater than the first width 142 such that the first 116 and second 118 sides extend away from each other with respect to the longitudinal axis 124 moving from the first terminal end 112 to the second terminal end 114.

The second end portion 134 of the main body 110 defines a slot 160. The slot 160 is a passageway that extends through the entire thickness 130 of the main body 110, from the first surface 120 to the second surface 122. In the illustrated embodiment, the slot 160 has a semi-circular shape and is sized to allow the first terminal end 112 and the first end portion 132 to be slidably passed through the slot 160 when the first terminal end 112 is passed back toward the second terminal end 114. The slot can have any suitable shape and a skilled artisan will be able to select an appropriate shape for a medical device according to a particular embodiment based on various considerations, including any desired ease with which the first terminal end of the medical device can be passed through the slot. The slot should be sized, however, such that the first terminal end and at least a portion of the first end portion of the medical device can be passed through the slot.

In the illustrated embodiment, the slot 160 is a semi-circular portion of a circle having a radius 162 that is less than the first width 142. Thus, the slot 160 has a maximum dimension measured along or parallel to the longitudinal axis 124 that is less than the first width 142. While other relative sizings of the maximum longitudinal dimension of the slot and the width of the main body at the first terminal end can be used in medical devices according to particular embodiments, this relative sizing in the illustrated embodiment is considered advantageous at least because it sets the slot 160 as a physical barrier to insertion of the first terminal end 112 into the slot in a twisted manner, which can ensure that the first terminal end 112 is inserted such that no twisting of the main body occurs when disposing the medical device around a tissue during use. Also in the illustrated embodiment, the slot 160 has a slot width 164 that extends orthogonally to the longitudinal axis 124 from the first slot side 166 to a second slot side 168. The slot 160 has a first slot edge 170 that is linear or substantially linear and a second slot edge 172 that defines an arc 174. The first slot edge 170 extends orthogonally to the longitudinal axis 124 and is disposed closer to the first terminal end 112 than the second slot edge 172, while the second slot edge 172 is disposed closer to the second terminal end 114 than the first slot edge 170.

The second end portion 134 defines a tab portion 180 extending between the second slot edge 172 and the second terminal end 114. In the illustrated embodiment, the tab portion 180 extends along the longitudinal axis 124 from the second slot edge 172 to the first 116 and second 118 sides and the second terminal end 114. As such, the tab portion 180 has a generally arcuate shape with flat portions provided by the sides 116, 118. The tab portion 180 has an axial length 182 extending along the longitudinal axis 124 that is greater than the radius 162 of the slot 180.

In the illustrated embodiment, the first 120 and second 122 surfaces of the main body 110 are substantially flat. It is noted, though, that it may be advantages to include one or more bumps, projections or other surface modifications on one or both of the surfaces 120, 122. Inclusion of such modifications may improve the handling of the medical device 100 during use.

FIGS. 4 and 5 illustrate the first example medical device 100 disposed around a palatopharyngeus muscle 200. The first terminal end 112 has been doubled back onto the medical device 100 and passed through the slot 160 such that the medical device 100 encircles the palatopharyngeus muscle 200. To achieve this positioning, the first terminal end 112 has been passed through the slot 160 and behind the tab portion 180. The medical device 100 has been cinched around the palatopharyngeus muscle 200 by pulling the first distal end 112 to snug the medical device 100 against the palatopharyngeus muscle 200. Also, the palatopharyngeus muscle has been moved from an original position 202, shown in phantom, in the direction indicated by arrow 204, to a new position 206 by pulling the first end portion 132 of the medical device 100 generally in the direction indicated by arrow 204. To maintain the new position 206 of the palatopharyngeus muscle 200, a suture 220 has been passed through a passageway 140c of the series of passageways 140, through a portion of an adjacent tissue 250, and knotted or otherwise fixed to secure the first end portion 132 against the adjacent tissue 250.

As best illustrated in FIG. 5, the cinching of the medical device 100 around the palatopharyngeus muscle 200 may create a void 270 bounded by the first 120 or upper surface of the medical device 100 and the outer surface 208 of the palatopharyngeus muscle 200. It is noted that the muscle may flatten or otherwise morph to fill or substantially fill the space created by the cinching of the medical device 100 around the palatopharyngeus muscle 200.

FIGS. 6 and 7 illustrate a second example medical device 300. The medical device 300 is similar to the medical device 100 described above, except as detailed below. Thus, the medical device 300 has a main body 310 comprising a substantially flat member extending from a first terminal end 312 to an opposing second terminal end 314 and having first 316 and second 318 opposing sides. The main body 310 has a first 320 or upper surface and an opposing second 322 or lower surface. The main body 310 has a lengthwise axis 324 and a transverse axis 326 that orthogonally intersects the lengthwise axis 324 at a longitudinal midpoint 328 disposed on the lengthwise axis 324. The main body has a thickness 330 measured from the first surface 320 to the opposing second surface 322. A first end portion 332 extends along the lengthwise axis 324, includes the first terminal end 312, and extends toward but not to the longitudinal midpoint 328. A second end portion 334 extends along the lengthwise axis 324, includes the second terminal end 314, and extends toward but not to the longitudinal midpoint 328. A middle portion 336 extends along the lengthwise axis 324, between the first end portion 332 and second end portion 334, and includes the longitudinal midpoint 328. The main body 310 defines a series of passageways 340. Each passageway of the series of passageways 340 extends through the entire thickness 330 of the main body 310, from the first surface 320 to the second surface 322. The main body 310 has a first width 342 at the first terminal end 312 that extends orthogonally to the longitudinal axis 324 from the first side 316 to the second side 318. The second terminal end 314 defines an arc 344 that extends from a first arc base 346 on the first side 316 to a second arc base 348 on the second side 318. The main body 310 has a second width 350 that extends orthogonally to the longitudinal axis 324 from the first arc base 346 on the first side 316 to the second arc base 348 on the second side 318. The second width 350 is greater than the first width 342 such that the first 316 and second 318 sides extend away from each other with respect to the longitudinal axis 324 moving from the first terminal end 312 to the second terminal end 314.

The second end portion 334 of the main body 310 defines a slot 360. The slot 360 is a passageway that extends through the entire thickness 330 of the main body 310, from the first surface 320 to the second surface 322.

The second end portion 334 defines a tab portion 380 extending between the second slot edge 372 and the second terminal end 314. The tab portion 380 has an axial length 382 extending along the longitudinal axis 324 that is greater than the radius 362 of the slot 380.

In this embodiment, tab portion 380 defines a tab passageway 390 that extends through the entire thickness 330 of main body 310 from the first surface 320 to the second surface 322. If included in a medical device according to a particular embodiment, a tab passageway can be included at any suitable location on the tab of the medical device. In the illustrated embodiment, tab passageway 390 is disposed on the longitudinal axis 324 of the medical device 300, with the center of the tab passageway 390 equidistant from the second slot edge 372 and the second terminal end 314. This positioning is considered advantageous at least because it maximizes the amount of material of the main body 310 between the tab passageway 390, the second terminal end 314, and the second slot edge 372. This is expected to provide beneficial engagement between a suture, the tab portion 380 and the first portion 332 of the medical device in use, as described in more detail below.

FIGS. 8 and 9 illustrate the second example medical device 300 disposed around a palatopharyngeus muscle 400. The first terminal end 312 has been doubled back onto the medical device 300 and passed through the slot 360 such that the medical device 300 encircles the palatopharyngeus muscle 400. To achieve this positioning, the first terminal end 312 has been passed through the slot 360 and behind the tab portion 380. The medical device 300 has been cinched around the palatopharyngeus muscle 400 by pulling the first distal end 312 to snug the medical device 300 against the palatopharyngeus muscle 400. Also, once, the palatopharyngeus muscle 400 has been moved from an original position 402, shown in phantom, in the direction indicated by arrow 404, to a new position 406 by pulling the first end portion 332 of the medical device 300 generally in the direction indicated by arrow 404. To maintain the new position 406 of the palatopharyngeus muscle 400, a suture 420 has been passed through a passageway 340c of the series of passageways 340, through a portion of an adjacent tissue 450, and knotted or otherwise fixed to secure the first end portion 332 against the adjacent tissue 450.

A second suture 460 has been passed through the tab passageway 390 and a passageway of the series of passageways 340 on the main body 310. As best illustrated in FIG. 9, this second suture 460 has been knotted or otherwise fixed to secure the second surface 322 in the tab portion 380 against the second surface 322 in the first end portion 332 of the main body 310. Also as best illustrated in FIG. 9, this securement provided by the second suture 460 allows the medical device 300 to be maintained in a position in which the void 470 bounded by the first 320 or upper surface of the medical device 300 and the outer surface 408 of the palatopharyngeus muscle 400 is smaller than the void 270 achieved with the first example medical device 100, as best illustrated in FIG. 5. This ability to secure the medical device 300 in a position having a relatively small void 470 is considered advantageous at least because it provides more contact surface area between the medical device 300 and the palatopharyngeus muscle 300. Furthermore, the inclusion of the tab passageway 390 is considered particularly advantageous for medical devices formed entirely or partially of remodelable materials at least because it enables contact between adjacent surfaces of the medical device 300, as best illustrated in FIG. 9, which is expected to aid remodeling efforts.

FIG. 10 illustrates a third example medical device 500. The medical device 500 is similar to the medical device 100 described above, except as detailed below. Thus, the medical device 500 has a main body 510 comprising a substantially flat member extending from a first terminal end 512 to an opposing second terminal end 514 and having first 516 and second 518 opposing sides. The main body 510 has a first 520 or upper surface and an opposing second or lower surface (not visible in FIG. 10). The main body 510 has a lengthwise axis 524 and a transverse axis 526 that orthogonally intersects the lengthwise axis 524 at a longitudinal midpoint 528 disposed on the lengthwise axis 524. The main body 510 has a thickness measured from the first surface 520 to the opposing second surface. A first end portion 532 extends along the lengthwise axis 524, includes the first terminal end 512, and extends toward but not to the longitudinal midpoint 528. A second end portion 534 extends along the lengthwise axis 524, includes the second terminal end 514, and extends toward but not to the longitudinal midpoint 528. A middle portion 536 extends along the lengthwise axis 524, between the first end portion 532 and second end portion 534, and includes the longitudinal midpoint 528. The main body 510 defines a series of passageways 540. Each passageway of the series of passageways 540 extends through the entire thickness 530 of the main body 510, from the first surface 520 to the second surface. The main body 510 has a first width 542 at the first terminal end 512 that extends orthogonally to the longitudinal axis 524 from the first side 516 to the second side 518. The second terminal end 514 defines an arc 544 that extends from a first arc base 546 on the first side 516 to a second arc base 548 on the second side 518. The main body 510 has a second width 550 that extends orthogonally to the longitudinal axis 524 from the first arc base 546 on the first side 516 to the second arc base 548 on the second side 518. The second width 550 is greater than the first width 542 such that the first 516 and second 518 sides extend away from each other with respect to the longitudinal axis 524 moving from the first terminal end 512 to the second terminal end 514.

The second end portion 534 of the main body 510 defines a slot 560. The slot 560 is a passageway that extends through the entire thickness of the main body 510, from the first surface 520 to the second surface. In the illustrated embodiment, the slot 560 is a semi-ovular, i.e., half oval, portion of an oval having a minor radius 562 that is less than the first width 542. Thus, the slot 560 has a maximum dimension measured along or parallel to the longitudinal axis 524 that is less than the first width 542. The slot 560 has a slot width 564 that extends orthogonally to the longitudinal axis 524 from the first slot side 566 to a second slot side 568. The slot 560 has a first slot edge 570 that is linear or substantially linear and a second slot edge 572 that defines an arc 574. The first slot edge 570 extends orthogonally to the longitudinal axis 524 and is disposed closer to the first terminal end 512 than the second slot edge 572, while the second slot edge 572 is disposed closer to the second terminal end 514 than the first slot edge 570.

The second end portion 534 defines a tab portion 580 extending between the second slot edge 572 and the second terminal end 514. In this embodiment, the tab portion 580 has an axial length 582 extending along the longitudinal axis 524 that is less than the radius 562 of the slot 560.

Each passageway of the series of passageways 540 extends through the entire thickness of the main body 510, from the first surface 520 to the second surface. In this embodiment, the series of passageways 540 includes first 540a, second 540b, third 540c, and fourth 540d passageways. Each of the first 540a, second 540b, third 540c, and fourth 540d passageways is disposed on the first end portion 532, while the middle portion 536 is free of passageways, and the second end portion 534 is free of passageways except for the slot 560. This structural configuration is considered particularly advantageous for medical devices, such as the illustrated example medical device 500, in which the tab portion 580 has an axial length 582 that is less than the radius of the slot 562 that extends along the longitudinal axis 524 of the medical device 500.

Figure 11:
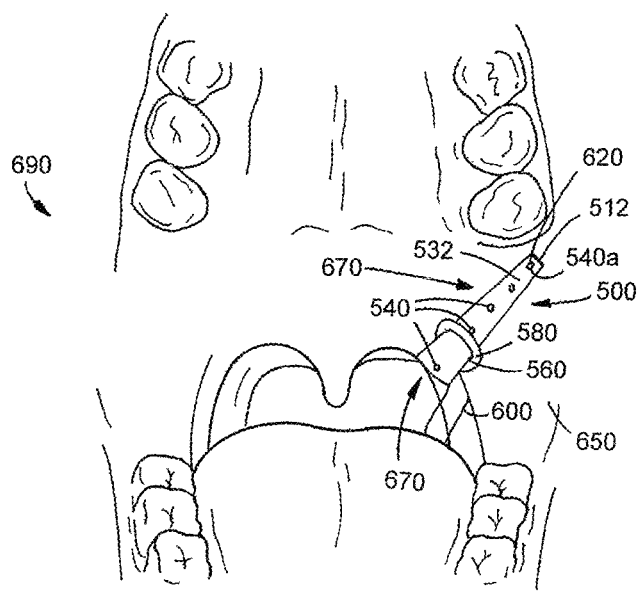
FIG. 11 is a frontal view of an oral cavity within which the third example medical device has been implanted.

FIG. 11 illustrates the third example medical device 500 disposed around a palatopharyngeus muscle 600 within an oral cavity 690 of a patient. The first terminal end 512 has been doubled back onto the medical device 500 and passed through the slot 560 such that the medical device 500 encircles the palatopharyngeus muscle 600. To achieve this positioning, the first terminal end 512 has been passed through the slot 560 and behind the tab portion 580. The medical device 500 has been cinched around the palatopharyngeus muscle 600 by pulling the first distal end 512 to snug the medical device 500 against the palatopharyngeus muscle 600. The palatopharyngeus muscle 600 has been moved from an original position to the desired new position illustrated in the Figure by pulling the first end portion 532 of the medical device 500. To maintain the new position of the palatopharyngeus muscle 600, a suture 620 has been passed through a passageway 540a of the series of passageways 540, through a portion of an adjacent tissue 650, and knotted or otherwise fixed to secure the first end portion 532 against the adjacent tissue 650. The first end portion 532 has been disposed within a tunnel 670 created in adjacent tissue 650 prior to placement of the suture 620 and, therefore, prior to fixation of the first end portion 532 of the medical device 500 to the adjacent tissue 650. The tunnel 670 can be a natural opening, cavity, passageway or other void in a tissue, or, as in the procedure illustrated in the Figure, can be an artificial tunnel created for the purpose of receiving the first end portion 532 of the medical device, such as a tunnel created by basic blunt dissection techniques.

Figure 12:
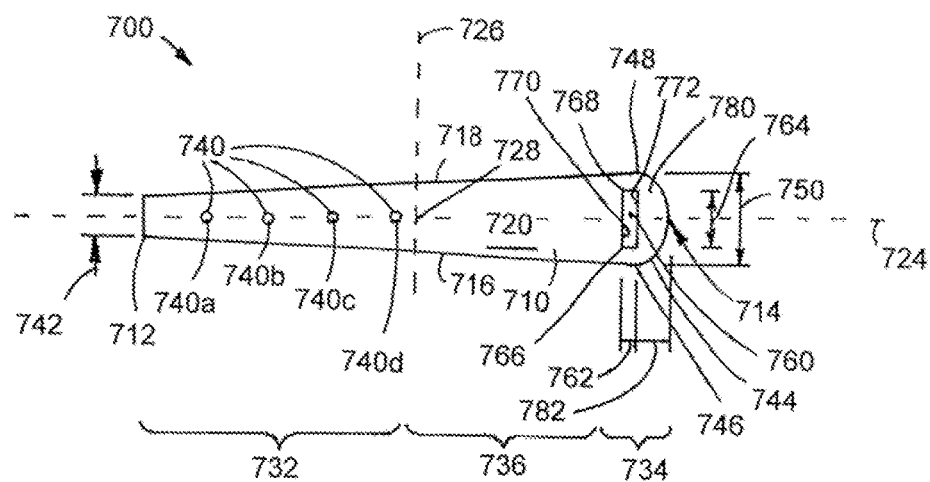
FIG. 12 is a top view of a fourth example medical device.

FIG. 12 illustrates a fourth example medical device 700. The medical device 700 is similar to the medical device 100 described above, except as detailed below. Thus, the medical device 700 has a main body 710 comprising a substantially flat member extending from a first terminal end 712 to an opposing second terminal end 714 and having first 716 and second 718 opposing sides. The main body 710 has a first 720 or upper surface and an opposing second or lower surface (not visible in FIG. 12). The main body 710 has a lengthwise axis 724 and a transverse axis 726 that orthogonally intersects the lengthwise axis 724 at a longitudinal midpoint 728 disposed on the lengthwise axis 724. The main body 710 has a thickness measured from the first surface 720 to the opposing second surface. A first end portion 732 extends along the lengthwise axis 724, includes the first terminal end 712, and extends toward but not to the longitudinal midpoint 728. A second end portion 734 extends along the lengthwise axis 724, includes the second terminal end 714, and extends toward but not to the longitudinal midpoint 728. A middle portion 736 extends along the lengthwise axis 724, between the first end portion 732 and second end portion 734, and includes the longitudinal midpoint 728. The main body 710 defines a series of passageways 740. Each passageway of the series of passageways 740 extends through the entire thickness of the main body 710, from the first surface 720 to the second surface. In this embodiment, the series of passageways 740 includes first 740a, second 740b, third 740c, and fourth 740d passageways.

The main body 710 has a first width 742 at the first terminal end 712 that extends orthogonally to the longitudinal axis 724 from the first side 716 to the second side 718. The second terminal end 714 defines an arc 744 that extends from a first arc base 746 on the first side 716 to a second arc base 748 on the second side 718. The main body 710 has a second width 750 that extends orthogonally to the longitudinal axis 724 from the first arc base 746 on the first side 716 to the second arc base 748 on the second side 718. The second width 750 is greater than the first width 742 such that the first 716 and second 718 sides extend away from each other with respect to the longitudinal axis 724 moving from the first terminal end 712 to the second terminal end 714.

The second end portion 734 of the main body 710 defines a slot 760. The slot 760 is a passageway that extends through the entire thickness of the main body 710, from the first surface 720 to the second surface. In the illustrated embodiment, the slot 760 is a rectangular opening having a minor width 762 that is less than the first width 742. Thus, the slot 760 has a maximum dimension measured along or parallel to the longitudinal axis 724 that is less than the first width 742. The slot 760 has a slot width 764 that extends orthogonally to the longitudinal axis 724 from the first slot side 766 to a second slot side 768. The slot 760 has first 770 and second 772 slot edges, each of which is linear or substantially linear. The first slot edge 770 extends orthogonally to the longitudinal axis 724 and is disposed closer to the first terminal end 712 than the second slot edge 772, while the second slot edge 772 is disposed closer to the second terminal end 714 than the first slot edge 770.

The second end portion 734 defines a tab portion 780 extending between the second slot edge 772 and the second terminal end 714. In this embodiment, the tab portion 780 has an axial length 782 extending along the longitudinal axis 724 that is greater than the minor width 762 of the rectangular slot 780. In embodiments in which the slot is rectangular, such as the example medical device 700 illustrated in FIG. 12, it is considered advantageous to include a tab portion 780 having an axial length 782 that is between about two and about three times the minor width 762 of the slot 760. In the illustrated embodiment, the tab portion 780 has an axial length 782 that is about 2.5 times the minor width 762 of the slot 760. This structural arrangement is considered particularly advantageous at least because it provides a balance between a desired ability to position the first terminal end 712 through the slot 760 and to minimize the profile of the medical device 700 following implantation.

Figure 13:
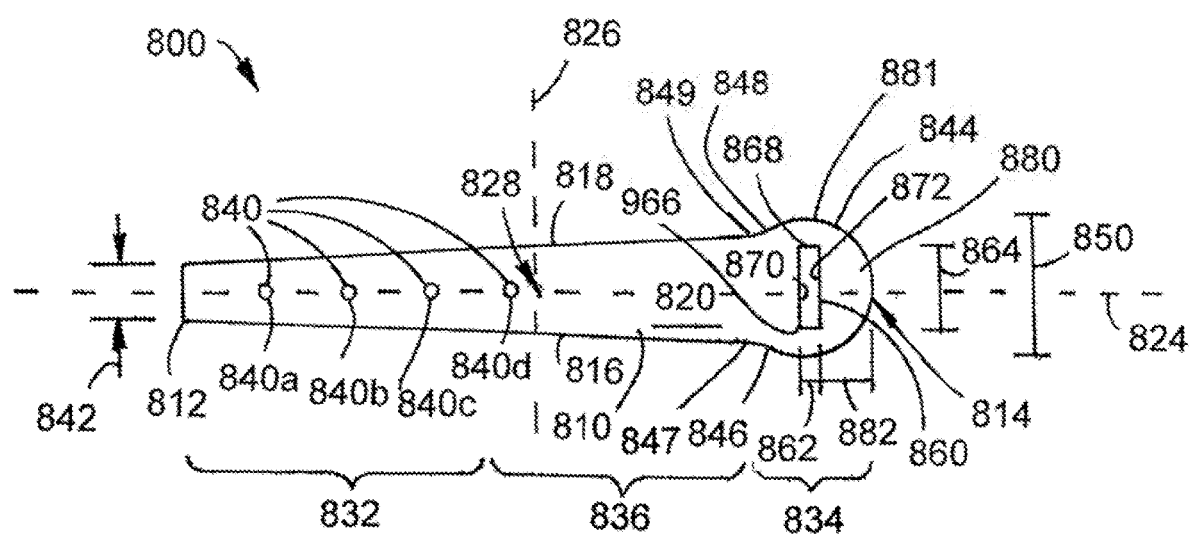
FIG. 13 is a top view of a fifth example medical device.
Figure 13A:
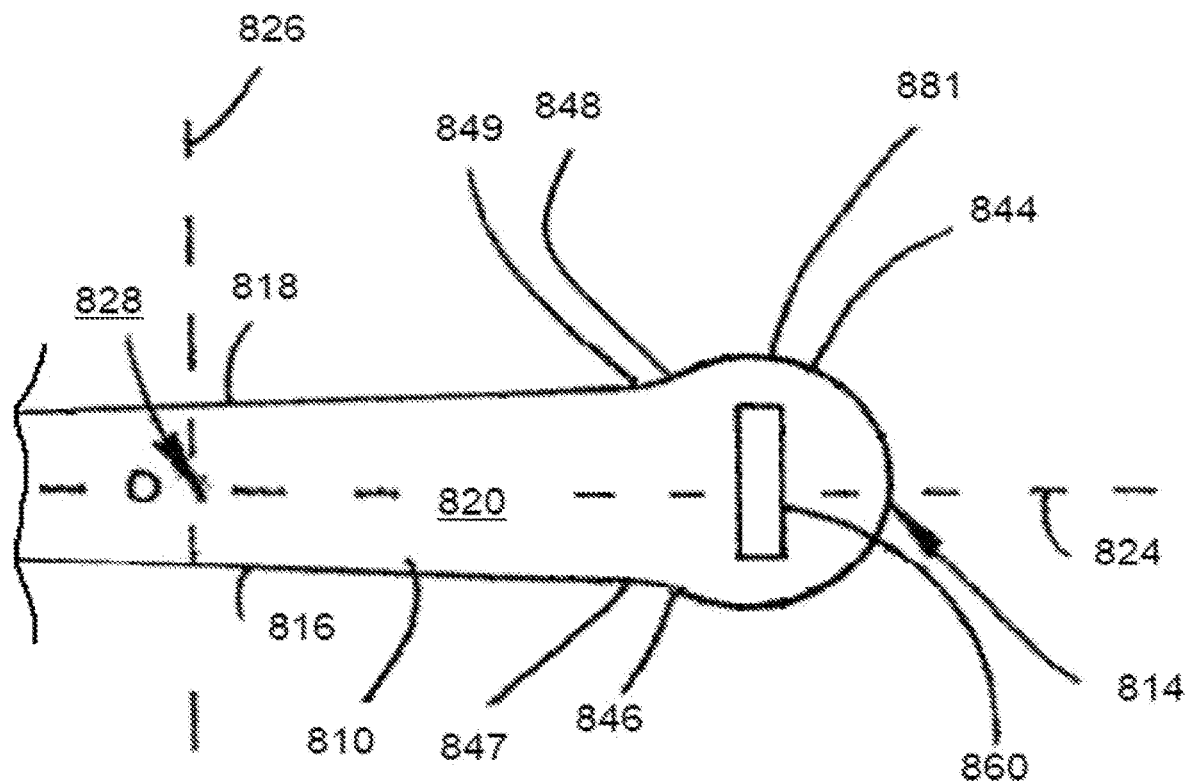
FIG. 13A is a magnified view of the second terminal end of the fifth example medical device illustrated in FIG. 13.

FIG. 13 illustrates a fifth example medical device 800. The medical device 800 is similar to the medical device 800 described above, except as detailed below. Thus, the medical device 800 has a main body 810 comprising a substantially flat member extending from a first terminal end 812 to an opposing second terminal end 814 and having first 816 and second 818 opposing sides. The main body 810 has a first 820 or upper surface and an opposing second or lower surface (not visible in FIG. 12). The main body 810 has a lengthwise axis 824 and a transverse axis 826 that orthogonally intersects the lengthwise axis 824 at a longitudinal midpoint 828 disposed on the lengthwise axis 824. The main body 810 has a thickness measured from the first surface 820 to the opposing second surface. A first end portion 832 extends along the lengthwise axis 824, includes the first terminal end 812, and extends toward but not to the longitudinal midpoint 828. A second end portion 834 extends along the lengthwise axis 824, includes the second terminal end 814, and extends toward but not to the longitudinal midpoint 828. A middle portion 836 extends along the lengthwise axis 824, between the first end portion 832 and second end portion 834, and includes the longitudinal midpoint 828. The main body 810 defines a series of passageways 840. Each passageway of the series of passageways 840 extends through the entire thickness of the main body 810, from the first surface 820 to the second surface. In this embodiment, the series of passageways 840 includes first 840a, second 840b, third 840c, and fourth 840d passageways.

The main body 810 has a first width 842 at the first terminal end 812 that extends orthogonally to the longitudinal axis 824 from the first side 816 to the second side 818. The second terminal end 814 defines an arc 844 that extends from a first arc base 846 on the first side 816 to a second arc base 848 on the second side 818. The main body 810 has a second width 850 that extends orthogonally to the longitudinal axis 824 from the arc 844 on the first side 816 to the arc 844 on the second side 818. The second width 850 is greater than the first width 842 such that the first 816 and second 818 sides extend away from each other with respect to the longitudinal axis 824 moving from the first terminal end 812 to the second terminal end 814.

The second end portion 834 of the main body 810 defines a slot 860. The slot 860 is a passageway that extends through the entire thickness of the main body 810, from the first surface 820 to the second surface. In the illustrated embodiment, the slot 860 is a rectangular opening having a minor width 862 that is less than the first width 842. Thus, the slot 860 has a maximum dimension measured along or parallel to the longitudinal axis 824 that is less than the first width 842. The slot 860 has a slot width 864 that extends orthogonally to the longitudinal axis 824 from the first slot side 866 to a second slot side 868. The slot 860 has first 870 and second 872 slot edges, each of which is linear or substantially linear. The first slot edge 870 extends orthogonally to the longitudinal axis 824 and is disposed closer to the first terminal end 812 than the second slot edge 872, while the second slot edge 872 is disposed closer to the second terminal end 814 than the first slot edge 870.

The second end portion 834 defines a tab portion 880 extending between the second slot edge 872 and the second terminal end 814. In this embodiment, the tab portion 880 has an axial length 882 extending along the longitudinal axis 824 that is greater than the minor width 862 of the rectangular slot 880. In the illustrated embodiment, the tab portion 880 has an axial length 882 that is about three times the minor width 862 of the slot 860.

In this embodiment, The second end portion 834 is bulbous-shaped such that the outer edge 881 is not a natural extension of the linear path of either side 816, 818 of the medical device 800. To achieve this structure, each of the first arc base 846 and second arc base 848 are disposed axially between the first slot edge 870 and the first terminal end 812. Furthermore, a first arc extension 847 extends from the first arc base 846 to the linear path of the first side 816 and a second arc extension 849 extends from the second arc base 848 to the linear path of the second side 818. This bulbous-shaped structural arrangement, is considered particularly advantageous at least because it provides an enhanced ability to snug the second end portion 834 against the palatopharyngeus muscle during implantation without adding significantly to the overall profile of the medical device 800.

Figure 14:
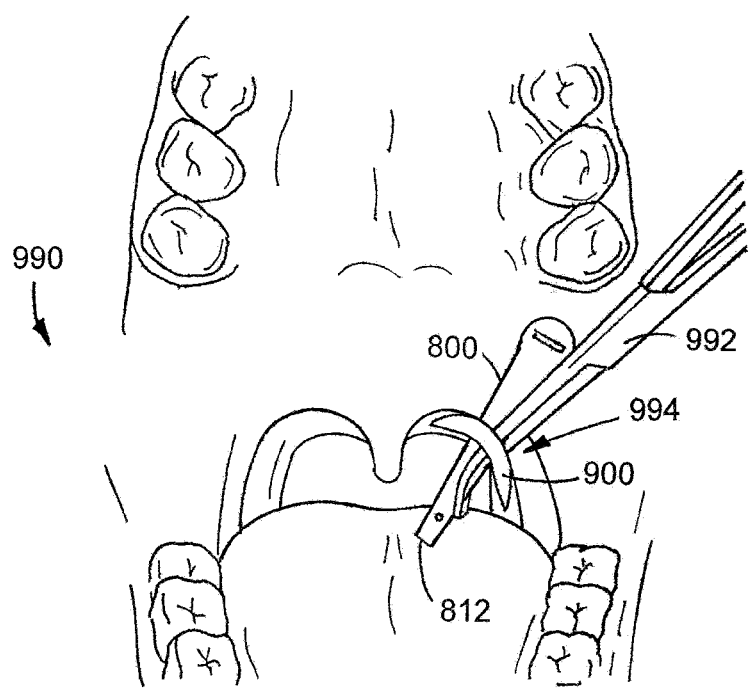
FIG. 14 is a frontal view of an oral cavity within which the fifth example medical device is being implanted.

FIG. 14 illustrates the fifth example medical device 800 disposed behind a palatopharyngeus muscle 900 within an oral cavity 990 of a patient during an implantation procedure. A user has used forceps 992 to maintain a clearance 994 behind the palatopharyngeus muscle 900 while the first terminal end 812 of the medical device 800 has been passed through the clearance 994. This represents an interim step in an implantation procedure.

Medical devices according to the invention are advantageously made from a pliable material, or a material that can be rendered pliable, to facilitate manipulation during implantation. A medical device according to a particular embodiment can be formed from any suitable material or materials, and using any suitable equipment and process or processes, and a skilled artisan will be able to select appropriate material(s), equipment, and process(es) for a medical device according to a particular embodiment based on various considerations, including the extent of any manipulation expected to be necessary or desirable during an implantation procedure.

A medical device according to the invention can be formed from a unitary section of material or as multiple sections of material secured to each other to form the medical device. For example, the inventors have determined that a medical device formed as a multilaminate construct, as described below, is considered advantageous.

Both synthetic and natural materials are considered suitable materials for forming medical devices according to embodiments of the invention. Examples of suitable synthetic materials include polymeric materials, such as polyethylene, polypropylene and other flexible polymeric materials. Examples of suitable natural materials include tissue and tissue-derived materials. The inventors have determined that medical devices formed of bioremodelable materials are particularly well-suited for medical devices according to embodiments of the invention at least because of the ability of such materials to remodel and become incorporated into adjacent tissues over time. These materials can provide a scaffold onto which cellular in-growth can occur, eventually allowing the material to remodel into a structure of host cells, which aids in the effectiveness of the medical device as a long-term support of the tissue being secured.

Particular advantage can be provided by medical devices that incorporate a remodelable collagenous material. Such remodelable collagenous materials, whether reconstituted or naturally-derived, can be provided, for example, by collagenous materials isolated from a warm-blooded vertebrate, especially a mammal. Such isolated collagenous material can be processed so as to have remodelable, angiogenic properties and promote cellular invasion and ingrowth. Remodelable materials may be used in this context to stimulate ingrowth of adjacent tissues into an implanted construct such that the remodelable material gradually breaks down and becomes replaced by new patient tissue so as to generate a new, remodeled tissue structure. Such materials are considered suitable for use in the main body, projections, and plug portions of medical devices. Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the medical devices, and their isolation and treatment, reference can be made, for example, to U.S. Pat. Nos. 4,902,508, 5,554,389, 5,993,844, 6,206,931, and 6,099,567.

Remodelable ECM tissue materials harvested as intact sheets from a mammalian source and processed to remove cellular debris advantageously retain at least a portion of and potentially all of the native collagen microarchitecture of the source extracellular matrix. This matrix of collagen fibers provides a scaffold to facilitate and support tissue ingrowth, particularly in bioactive ECM implant materials, such as porcine small intestinal submucosa or SIS (Biodesign™, Cook Medical, Bloomington Ind.), that are processed to retain an effective level of growth factors and other bioactive constituents from the source tissue. In this regard, when a medical device incorporates this sort of material, cells will invade the remodelable material upon implantation eventually leading to the generation of a newly-remodeled, functional tissue structure.

Submucosa-containing or other ECM tissue used in medical devices according to embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the inventive medical devices.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source. In a dry state, a typical layer thickness for an as-isolated submucosa or other ECM tissue layer used in the invention ranges from about 10 to about 160 microns when fully dry, more typically from about 15 to about 130 microns when fully dry.

A medical device according to an embodiment of the invention can include one or more bioactive agents, such as in a coating or as an integrated component. Suitable bioactive agents may include one or more bioactive agents native to the source of an ECM tissue material used in the medical device. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials used in a medical device according to an embodiment can be derived from any suitable organ or other tissue source, usually sources containing connective tissues. The ECM materials processed for use in the inventive medical devices will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

When used in medical devices according to embodiments of the invention, submucosa-containing or other ECM material may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material used in a medical device according to an embodiment of the invention. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Medical devices according to embodiments of the invention can incorporate xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogeneic relative to the ECM material) or may be from a different species from the ECM material source (xenogeneic relative to the ECM material). In certain embodiments, ECM material will be xenogeneic relative to the patient receiving the graft, and any added exogenous material(s) will be from the same species (e.g. autologous or allogeneic) as the patient receiving the graft. Illustratively, human patients may be treated with xenogeneic ECM materials (e.g. porcine-, bovine- or ovine-derived) that have been modified with exogenous human material(s) as described herein, those exogenous materials being naturally derived and/or recombinantly produced.

The inventors have determined that SIS is particularly well-suited for use in medical devices according to the embodiments of the invention at least because of its well-characterized nature and ready availability. Furthermore, the inventors have determined that vacuum-pressed SIS provides a particularly advantageous material from which to form medical devices according to embodiments of the invention. Lyophilized SIS can also be used, and may be advantageous for medical devices for which a relatively quicker remodeling time is desired. Radiopaque SIS can also be used, and may be advantageous for medical devices for which enhanced visualization characteristics are desired.

The inventors have determined that a medical devices formed of multiple layers laminated together provides a particularly advantageous structure. Thus, the main body can comprise a multilaminate construct. In these embodiments, any suitable number of layers can be used, and a skilled artisan will be able to select an appropriate number of layers for a particular medical device based on various considerations, including the intended use of the medical device and nature of the tissue intended to be supported by the medical device. The inventors have determined that a medical device formed of between 4 and 15 layers of an ECM material, such as SIS, provides a particularly advantageous structure for medical devices according to embodiments of the invention. A medical device formed of between 8 and 12 layers of an ECM material, such as SIS, is also considered particularly advantageous. A medical device formed of 12 layers of an ECM material, such as SIS, is also considered particularly advantageous. A medical device formed of up to 60 layers of an ECM material, such as SIS, is also considered particularly advantageous. In these embodiments, the layers can be assembled together in any suitable manner and using any suitable technique or process. For multilaminate SIS constructs, the inventors have determined that vacuum-pressing of multiple layers of SIS provides a suitable laminate structure for use as a medical device as described herein. The layers in the multilaminate construct can be vacuum-pressed prior to assembly into the multilaminate construct. Alternatively, the multilaminate construct can be vacuum-pressed after assembly of the layers. In these embodiments, the layers are advantageously non-vacuum pressed prior to assembly into the multilaminate construct. Also alternatively, the layers can be vacuum-pressed prior to assembly and the assembly can be vacuum-pressed after assembly. The inventors have determined that a medical device formed of about 12 layers of SIS, vacuum-pressed only after layer assembly, provides a medical device having desirable durability, profile, handling, and performance characteristics. The inventors have determined that use of vacuum-pressed layers of SIS can also provide desirable characteristics. When using vacuum-pressed layers of an ECM material, such as SIS, any suitable number of vacuum-pressed layers can be used. The inventors have determined that a medical device formed of between 4 and 60 vacuum-pressed layers provides a particularly advantageous structure for medical devices according to embodiments of the invention. A medical device formed of between 10 and 50 vacuum-pressed layers is also considered particularly advantageous. A medical device formed of between 10 and 30 vacuum-pressed layers is also considered particularly advantageous. A medical device formed of between 10 and 20 vacuum-pressed layers is also considered particularly advantageous.

A hybrid structure in which a mesh is embedded inside an SIS or other composition or between layers of SIS or of other material is also considered suitable. For example, a polymeric mesh, such as a mesh formed of polypropylene, can be disposed between layers of SIS during formation of a medical device according to an embodiment. In these embodiments, the polymeric mesh will remain in the body following completion of remodeling by the SIS, which may enhance the overall anchoring of the supported tissue over time. A bioabsorbable mesh, such as a mesh formed of polyglycolic acid or other bioabsorbable material, can also be included in the medical device in this manner and may be advantageous where supplemental support is desired that lasts beyond the remodeling time for the SIS, but that does not have the permanency associated with a polypropylene or other polymeric mesh. Examples of suitable structural arrangements of polymer and remodelable layers can be found in United States Patent Application Publication No. 2011/0166673 to Patel et al., for QUILTED IMPLANTABLE GRAFT, the entire contents of which are hereby incorporated into this disclosure.

Medical devices according to an embodiment, or portions thereof, can also be coated with particular materials to provide a desired property or properties. For example, the inventors have determined that coating a medical device with poly(lactic-co-glycolic acid) (PLGA) provides a desirable stiffening effect to the implant while also providing an agent that promotes an inflammatory response in tissue within which the medical device has been placed. In medical devices that comprise a multilaminate construct, as describe above, a coating can be applied between layers during fabrication. For example, PLGA can be applied to or embedded within one, two, a plurality of, or all of the layers when making a medical device that comprise a multilaminate construct.

Figure 15:
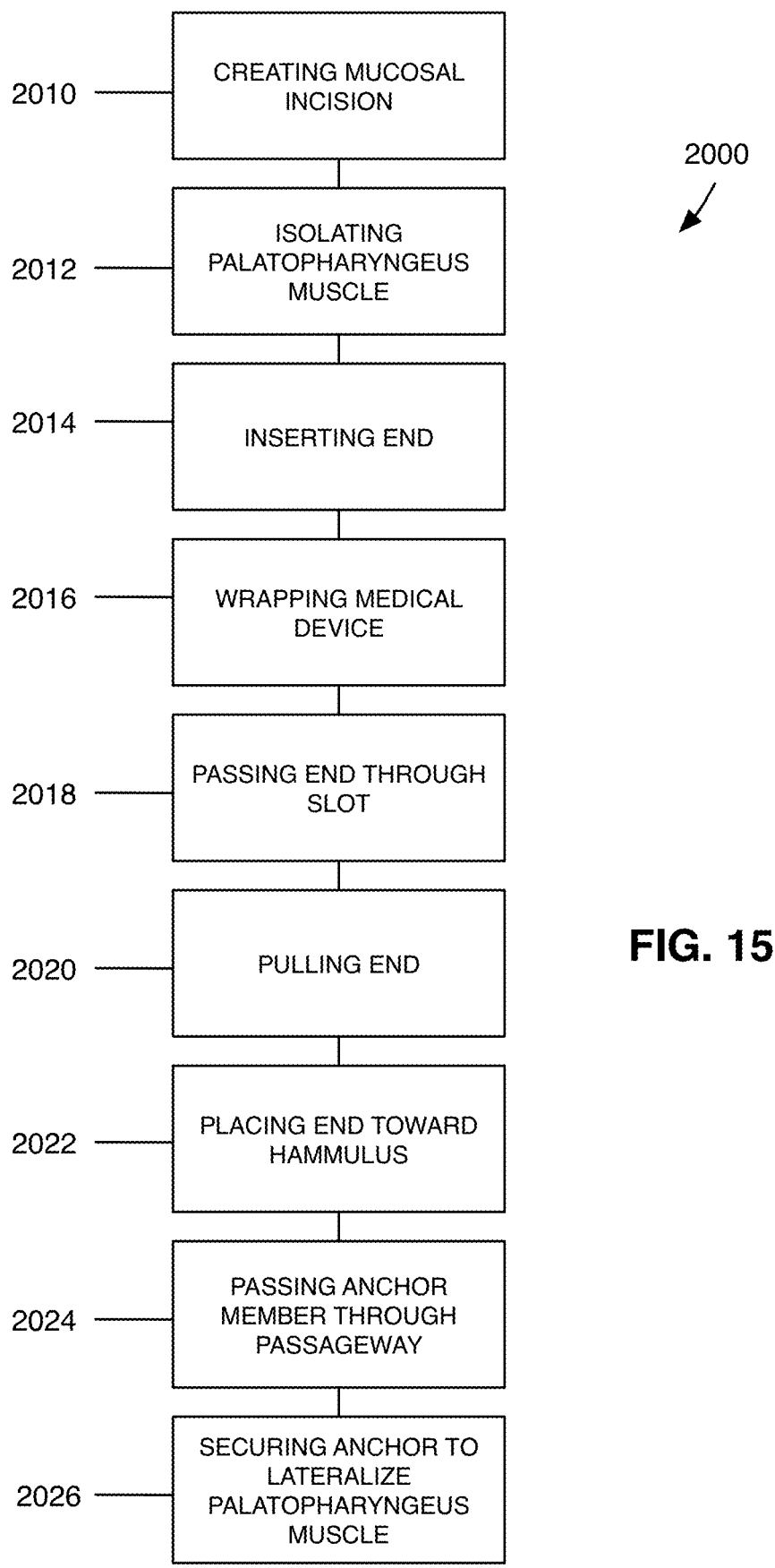
FIG. 15 is a flowchart illustration of an example method of treating obstructive sleep apnea.

FIG. 15 is a flowchart illustration of an example method 2000 of treating obstructive sleep apnea. An initial step 2010 comprises creating a mucosal incision in the arch of the posterior tonsillar pillar to expose the palatopharyngeus muscle. Another step 2012 comprises isolating the palatopharyngeus muscle to create a clearance behind the palatopharyngeus muscle. It is considered advantageous to create a clearance of between about 0.50 cm and about 1 cm behind the palatopharyngeus muscle. Creation of a clearance of about 0.75 cm behind the palatopharyngeus muscle is considered particularly advantageous for this step. Another step 2014 comprises inserting one end of a medical device according to an embodiment into the clearance created in step 2012. Another step 2016 comprises wrapping the medical device around the palatopharyngeus muscle. Another step 2018 comprises passing one end of the medical device through the slot of the medical device. Another step 2020 comprises pulling one end of the medical device to create a snug fit of the medical device around the palatopharyngeus muscle. Another step 2022 comprises placing the end of the medical device that was passed through the slot in step 2018 into the palatoglossus muscle toward the hammulus. Another step 2024 comprises passing an anchor member, such as a suture, through a passageway through the main body of the medical device. Another step 2026 comprises securing the anchor member to tissue to lateralize the palatopharyngeus muscle.

Figure 16:
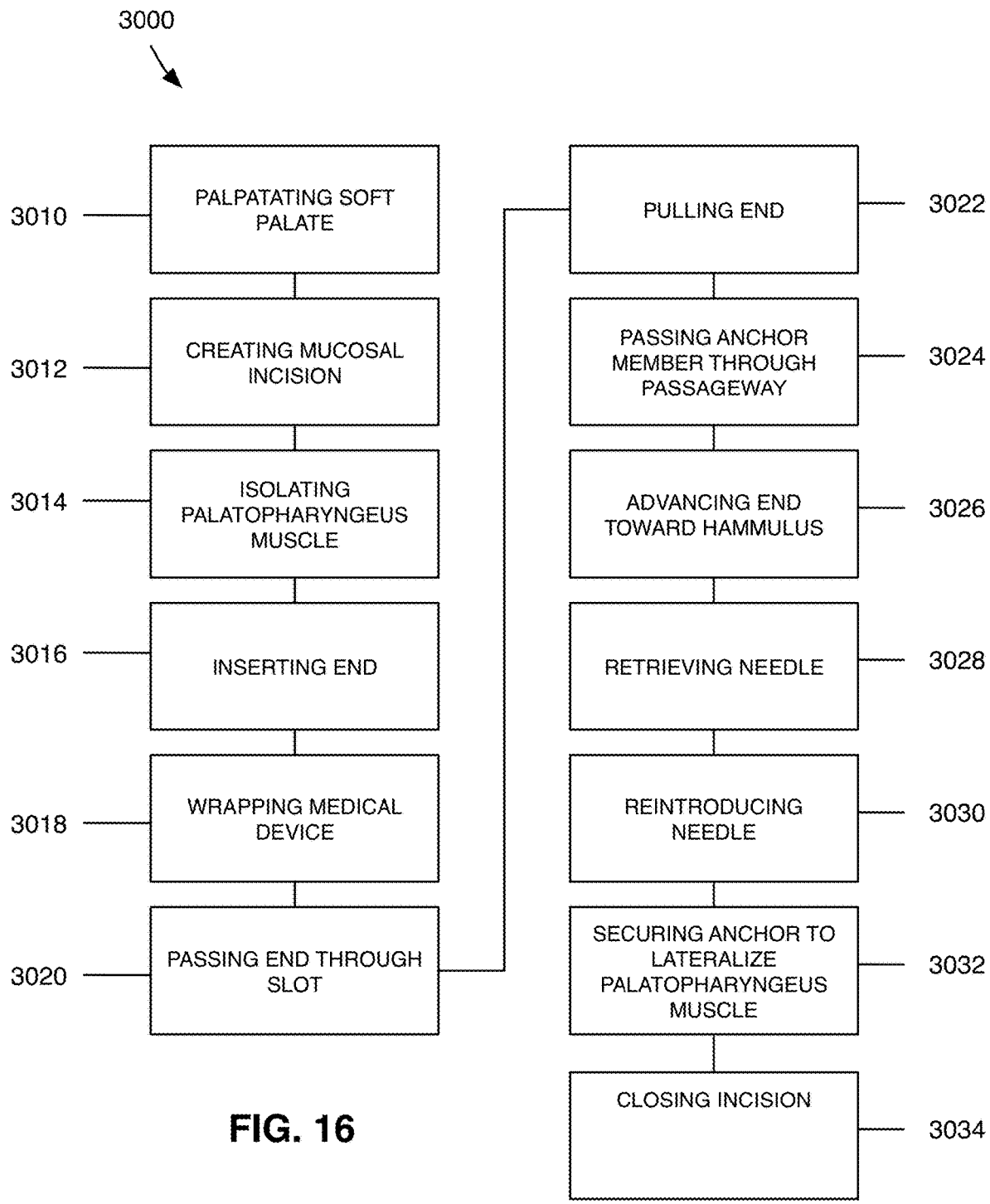
FIG. 16 is a flowchart illustration of another example method of treating obstructive sleep apnea.
Figure 17:
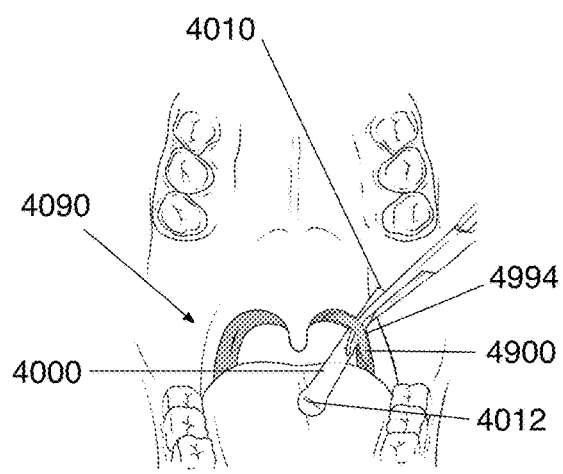
FIG. 17 is a frontal view of an oral cavity within which an example medical device is being implanted.

FIG. 16 is a flowchart illustration of an example method 3000 of treating obstructive sleep apnea. An initial step 3010 comprises palpating the soft palate to ensure no evidence of a submucosal cleft is found. Another step 3012 comprises creating a mucosal incision in the arch of the posterior tonsillar pillar to expose the palatopharyngeus muscle. Another step 3014 comprises isolating the palatopharyngeus muscle to create a clearance behind the palatopharyngeus muscle. Another step 3016 comprises inserting one end of a medical device according to an embodiment into to the clearance that was created in step 3014. Another step 3018 comprises wrapping the medical device around the palatopharyngeus muscle. Another step 3020 comprises passing one end of the medical device through the slot of the medical device. Another step 3022 comprises pulling one end of the medical device to create a snug fit of the medical device around the palatopharyngeus muscle. Another step 3024 comprises passing an anchor member, such as a suture, through a passageway through the main body of the medical device near the narrow end of the medical device. Another step 3026 comprises advancing the narrow end of the medical device deep to the palatoglossus muscle toward the hammulus. Another step 3028 comprises retrieving a needle from the mucosa overlying the hammulus. Another step 3030 comprises reintroducing the needle into the mucosa and tunneling medially in the submucosa toward the mucosal incision. Another step 3032 comprises securing the anchor member to tissue to lateralize the palatopharyngeus muscle. Another step 3034 comprises closing the incision with a suitable closure device, such as one or more sutures. The method 3000 can include repetition of all steps on an opposite side of the oral cavity of a patient to implant a second medical device if desired. Additionally, an optional step of injecting long acting anesthetic into the soft tissue as required can be included. In one alternative method, an additional step comprises creating a second mucosal incision to better visualize the anchor site. In this method, the step 3032 of securing the anchor member can be performed such that the anchor is secured at that second mucosal incision. To complete this method, the step 3034 of closing the incision comprises closing both incisions with a suitable closure device, such as sutures.

Figure 18:
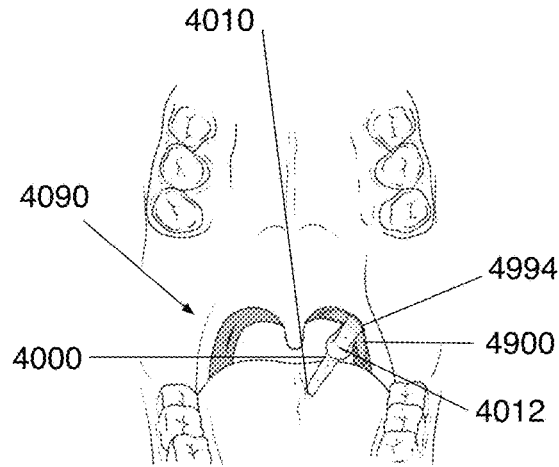
FIG. 18 is a frontal view of an oral cavity within which an example medical device is being implanted.
Figure 19:
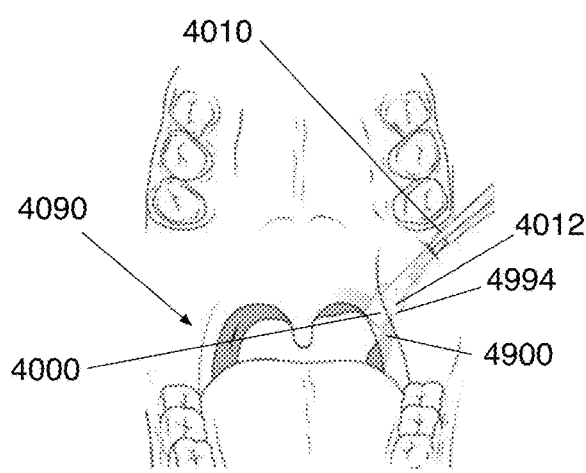
FIG. 19 is a frontal view of an oral cavity within which an example medical device is being implanted.
Figure 20:
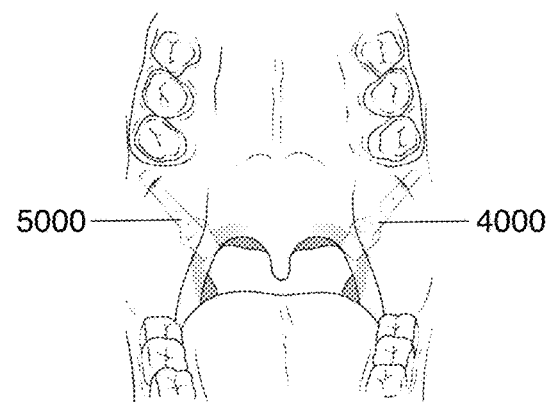
FIG. 20 is a frontal view of an oral cavity within which an example medical device is being implanted.

Each of FIGS. 17 through 20 illustrates a medical device 4000 according to an embodiment within an oral cavity 4090 of a patient during a stage of an implantation procedure conducted according to a method of treating obstructive sleep apnea in accordance with an embodiment. For example, in FIG. 17, one end 4010 of the medical device 4000 has been inserted into a clearance 4994 created behind the palatopharyngeus muscle 4900. In FIG. 18, the medical device 4000 has been wrapped around the palatopharyngeus muscle 4900 and one end 4010 of the medical device 4000 has been passed through the slot 4012 of the medical device 4000. In FIG. 19, the end 4010 of the medical device 4000 that was passed through the slot 4012 has been placed into the palatoglossus muscle toward the hammulus. FIG. 20 illustrates the oral cavity 4090 after completion of the procedure in which the medical device 4000 and a second medical device 5000 were implanted.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

We claim:

1. A medical device for repositioning tissue within an animal, comprising:
a main body having a lengthwise axis, a first terminal end, an opposing second terminal end, a first side, a second opposing side, a first surface, a second opposing surface, and a longitudinal midpoint disposed on the lengthwise axis between the first terminal end and the second terminal end and between the first side and the second opposing side, the second terminal end defining an arc that extends from a first arc base on the first side to a second arc base on the second opposing side, the main body having a first width at the first terminal end extending orthogonally to the lengthwise axis from the first side to the second opposing side, and a second width extending orthogonally to the lengthwise axis from the first arc base on the first side to the second arc base on the second opposing side, the second width being greater than the first width such that the first side and the second opposing side continuously extend away from each other with respect to the lengthwise axis starting from the first terminal end to a location disposed between the longitudinal midpoint and the second terminal end;
the main body defining a first end portion extending along the lengthwise axis from the first terminal end toward but not to the longitudinal midpoint, a second end portion extending along the lengthwise axis from the second terminal end toward but not to the longitudinal midpoint, and a middle portion extending along the lengthwise axis between the first end portion and second end portion and including the longitudinal midpoint;
the first end portion of the main body defining a series of passageways, each passageway of the series of passageways extending through the main body from the first surface to the second opposing surface; and
the second end portion of the main body defining a bulbous shape, a slot extending through the main body from the first surface to the second opposing surface and having a first slot edge and a second slot edge, and a tab portion extending between the second slot edge and the second terminal end of the main body, the slot having a minor width and a major width, the minor width being less than the first width, the tab portion having an axial length extending along the lengthwise axis that is greater than the minor width of the slot;
wherein each of the first arc base and the second arc base is disposed between the first slot edge and the first terminal end.

2. The medical device of claim 1, wherein the slot is a rectangular opening in the main body.

3. The medical device of claim 1, wherein the axial length is between about two and about three times the minor width of the slot.

4. The medical device of claim 1, wherein the axial length is about 2.5 times the minor width of the slot.

5. The medical device of claim 1, wherein the axial length is about three times the minor width of the slot.

6. The medical device of claim 1, wherein the middle portion of the main body is free of openings that extend from the first surface to the second opposing surface.

7. The medical device of claim 1, wherein the series of passageways comprises four passageways.

8. The medical device of claim 1, wherein the main body is formed of a pliable material.

9. The medical device of claim 1, wherein the main body is formed of a bioremodelable material.

10. The medical device of claim 9, wherein the bioremodelable material comprises an extracellular matrix (ECM) material.

11. The medical device of claim 10, wherein the extracellular matrix material comprises small intestinal submucosa (SIS).

12. The medical device of claim 1, wherein said medical device comprises an integral, multilaminate construct comprising layers of small intestinal submucosa (SIS).

13. The medical device of claim 12, wherein the multilaminate construct comprises a construct of between 4 and 15 layers of SIS.

14. The medical device of claim 12, wherein the multilaminate construct comprises a construct of between 8 and 12 layers of SIS.

15. The medical device of claim 12, wherein the multilaminate construct comprises a construct of 12 layers of SIS.

16. The medical device of claim 12, wherein the multilaminate construct is vacuum-pressed.

17. The medical device of claim 16, wherein the layers of SIS are not vacuum-pressed prior to assembly into the multilaminate construct.

18. A medical device for repositioning tissue within an animal, comprising:
a main body having a lengthwise axis, a first terminal end, an opposing second terminal end, a first side, a second opposing side, a first surface, a second opposing surface, and a longitudinal midpoint disposed on the lengthwise axis between the first terminal end and the second terminal end and between the first side and the second opposing side, the second terminal end defining an arc that extends from a first arc base on the first side to a second arc base on the second opposing side, the main body having a first width at the first terminal end extending orthogonally to the lengthwise axis from the first side to the second opposing side, and a second width extending orthogonally to the lengthwise axis from the first arc base on the first side to the second arc base on the second opposing side, the second width being greater than the first width such that the first side and the second opposing side continuously extend away from each other with respect to the lengthwise axis starting from the first terminal end to a location disposed between the longitudinal midpoint and the second terminal end;

the main body defining a first end portion extending along the lengthwise axis from the first terminal end toward but not to the longitudinal midpoint, a second end portion extending along the lengthwise axis from the second terminal end toward but not to the longitudinal midpoint, and a middle portion extending along the lengthwise axis between the first end portion and second end portion and including the longitudinal midpoint;

the first end portion of the main body defining a series of passageways, each passageway of the series of passageways extending through the main body from the first surface to the second opposing surface;

the second end portion of the main body defining a bulbous shape, a rectangular slot extending through the main body from the first surface to the second opposing surface and having a first slot edge and a second slot edge, and a tab portion extending between the second slot edge and the second terminal end of the main body, the rectangular slot having a minor width and a major width, the minor width being less than the first width, the tab portion having an axial length extending along the lengthwise axis that is greater than the minor width of the rectangular slot; and the main body comprising an integral, vacuum-pressed multilaminate construct comprising between 4 and 15 layers of small intestinal submucosa;

wherein the layers of small intestinal submucosa are not vacuum-pressed prior to assembly into the multilaminate construct; and wherein each of the first arc base and the second arc base is disposed between the first slot edge and the first terminal end.

19. The medical device of claim 18, wherein the axial length is between about two and about three times the minor width of the rectangular slot.

20. A medical device for repositioning tissue within an animal, comprising:

a main body having a lengthwise axis, a first terminal end, an opposing second terminal end, a first side, a second opposing side, a first surface, a second opposing surface, and a longitudinal midpoint disposed on the lengthwise axis between the first terminal end and the second terminal end and between the first side and the second opposing side, the second terminal end defining an arc that extends from a first arc base on the first side to a second arc base on the second opposing side, the main body having a first width at the first terminal end extending orthogonally to the lengthwise axis from the first side to the second opposing side, and a second width extending orthogonally to the lengthwise axis from the first arc base on the first side to the second arc base on the second opposing side, the second width being greater than the first width such that the first side and the second opposing side continuously extend away from each other with respect to the lengthwise axis starting from the first terminal end to a location disposed between the longitudinal midpoint and the second terminal end;

the main body defining a first end portion extending along the lengthwise axis from the first terminal end toward but not to the longitudinal midpoint, a second end portion extending along the lengthwise axis from the second terminal end toward but not to the longitudinal midpoint, and a middle portion extending along the lengthwise axis between the first end portion and second end portion and including the longitudinal midpoint;

the first end portion of the main body defining a series of passageways, each passageway of the series of passageways extending through the main body from the first surface to the second opposing surface;

the second end portion of the main body defining a bulbous shape, a rectangular slot extending through the main body from the first surface to the second opposing surface and having a first slot edge and a second slot edge, and a tab portion extending between the second slot edge and the second terminal end of the main body, the rectangular slot having a minor width and a major width, the minor width being less than the first width, the tab portion having an axial length extending along the lengthwise axis that is between about two and about three times the minor width of the rectangular slot, the second end portion of the main body is free of openings that extend from the first surface to the second opposing surface; and the main body comprising an integral, vacuum-pressed multilaminate construct comprising between 4 and 15 layers of small intestinal submucosa;

wherein the layers of small intestinal submucosa are not vacuum-pressed prior to assembly into the multilaminate construct; and wherein each of the first arc base and the second arc base is disposed between the first slot edge and the first terminal end.

21. The medical device of claim 1, wherein the second end portion of the main body is free of openings that extend from the first surface to the second opposing surface.

* * * * *